United States Patent
Koike

(10) Patent No.: US 12,307,664 B2
(45) Date of Patent: *May 20, 2025

(54) IMAGE PROCESSING DEVICE, IMAGE PROCESSING METHOD, AND IMAGE PROCESSING PROGRAM

(71) Applicant: FUJIFILM CORPORATION, Tokyo (JP)

(72) Inventor: Takafumi Koike, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 339 days.

This patent is subject to a terminal disclaimer.

(21) Appl. No.: 17/820,247

(22) Filed: Aug. 17, 2022

(65) Prior Publication Data

US 2022/0392064 A1     Dec. 8, 2022

Related U.S. Application Data

(63) Continuation of application No. PCT/JP2021/004848, filed on Feb. 9, 2021.

(30) Foreign Application Priority Data

Mar. 18, 2020   (JP) ................... 2020-047342

(51) Int. Cl.
*A61B 6/50*     (2024.01)
*A61B 6/00*     (2024.01)
(Continued)

(52) U.S. Cl.
CPC .......... *G06T 7/0012* (2013.01); *G06T 11/008* (2013.01); *G06T 2207/10112* (2013.01); *G06T 2207/30096* (2013.01)

(58) Field of Classification Search
CPC ................ G06T 7/0012; G06T 11/008; G06T 2207/10112; G06T 2207/30096;
(Continued)

(56) References Cited

U.S. PATENT DOCUMENTS

| | | | |
|---|---|---|---|
| 8,983,156 | B2 | 3/2015 | Periaswamy et al. |
| 9,792,703 | B2 | 10/2017 | Costa et al. |

(Continued)

FOREIGN PATENT DOCUMENTS

| | | | |
|---|---|---|---|
| CN | 102824184 | A | 12/2012 |
| CN | 104968272 | A | 10/2015 |

(Continued)

OTHER PUBLICATIONS

International Search Report issued in International Application No. PCT/JP2021/004848 on Apr. 20, 2021.

(Continued)

*Primary Examiner* — Amandeep Saini
*Assistant Examiner* — Emma Rose Goebel
(74) *Attorney, Agent, or Firm* — SOLARIS Intellectual Property Group, PLLC

(57) ABSTRACT

A processor detects a structure of interest from a plurality of tomographic images indicating a plurality of tomographic planes of an object. The processor selects a tomographic image from the plurality of tomographic images according to a frequency band in a region in which the structure of interest has been detected. The processor generates a composite two-dimensional image using the selected tomographic image in the region in which the structure of interest has been detected and using a predetermined tomographic image in a region in which the structure of interest has not been detected.

21 Claims, 29 Drawing Sheets

(51) Int. Cl.
*A61B 6/02* (2006.01)
*A61B 6/03* (2006.01)
*G06T 1/00* (2006.01)
*G06T 7/00* (2017.01)
*G06T 11/00* (2006.01)

(58) Field of Classification Search
CPC ..... G06T 2211/436; G06T 1/00; A61B 6/502; A61B 6/025; A61B 6/032; A61B 6/5205
See application file for complete search history.

(56) References Cited

U.S. PATENT DOCUMENTS

| | | |
|---|---|---|
| 2004/0101095 A1 | 5/2004 | Jing et al. |
| 2005/0113681 A1 | 5/2005 | Defreitas et al. |
| 2006/0098855 A1 | 5/2006 | Gkanatsios et al. |
| 2007/0030949 A1 | 2/2007 | Jing et al. |
| 2008/0019581 A1 | 1/2008 | Gkanatsios et al. |
| 2008/0130979 A1 | 6/2008 | Ren et al. |
| 2009/0003519 A1 | 1/2009 | Defreitas et al. |
| 2009/0010384 A1 | 1/2009 | Jing et al. |
| 2009/0123052 A1 | 5/2009 | Ruth et al. |
| 2009/0141859 A1 | 6/2009 | Gkanatsios et al. |
| 2009/0213987 A1 | 8/2009 | Stein et al. |
| 2009/0268865 A1 | 10/2009 | Ren et al. |
| 2009/0296882 A1 | 12/2009 | Gkanatsios et al. |
| 2010/0135456 A1 | 6/2010 | Jing et al. |
| 2010/0135558 A1 | 6/2010 | Ruth et al. |
| 2010/0195882 A1 | 8/2010 | Ren et al. |
| 2011/0069808 A1 | 3/2011 | Defreitas et al. |
| 2011/0069809 A1 | 3/2011 | Defreitas et al. |
| 2011/0135185 A1 | 6/2011 | Gkanatsios et al. |
| 2011/0216879 A1 | 9/2011 | Jing et al. |
| 2012/0195484 A1 | 8/2012 | Ren et al. |
| 2012/0219111 A1 | 8/2012 | Defreitas et al. |
| 2012/0321034 A1 | 12/2012 | Nakayama |
| 2013/0028374 A1 | 1/2013 | Gkanatsios et al. |
| 2013/0223591 A1 | 8/2013 | Jing et al. |
| 2013/0272494 A1 | 10/2013 | Defreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0232752 A1 | 8/2014 | Ren et al. |
| 2014/0301529 A1 | 10/2014 | Ren et al. |
| 2014/0327702 A1* | 11/2014 | Kreeger ................ G09G 5/377 382/131 |
| 2014/0376690 A1 | 12/2014 | Jing et al. |
| 2015/0049859 A1 | 2/2015 | Defreitas et al. |
| 2015/0052471 A1 | 2/2015 | Chen et al. |
| 2015/0160848 A1 | 6/2015 | Gkanatsios et al. |
| 2015/0182181 A1 | 7/2015 | Ruth et al. |
| 2015/0310611 A1 | 10/2015 | Gkanatsios et al. |
| 2015/0317538 A1 | 11/2015 | Ren et al. |
| 2015/0363904 A1 | 12/2015 | Arai et al. |
| 2016/0051215 A1 | 2/2016 | Chen et al. |
| 2016/0220210 A1 | 8/2016 | Ruth et al. |
| 2017/0011534 A1 | 1/2017 | Costa et al. |
| 2017/0024113 A1 | 1/2017 | Gkanatsios et al. |
| 2017/0128028 A1 | 5/2017 | Defreitas et al. |
| 2017/0135650 A1 | 5/2017 | Stein et al. |
| 2017/0316588 A1 | 11/2017 | Homann et al. |
| 2018/0047211 A1 | 2/2018 | Chen et al. |
| 2018/0055459 A1* | 3/2018 | Fukuda ................ A61B 6/5205 |
| 2018/0055470 A1 | 3/2018 | Ruth et al. |
| 2018/0068442 A1* | 3/2018 | Kawamura ........... G06T 7/0012 |
| 2018/0137385 A1 | 5/2018 | Ren et al. |
| 2018/0177476 A1 | 6/2018 | Jing et al. |
| 2018/0188937 A1 | 7/2018 | Gkanatsios et al. |
| 2018/0289347 A1 | 10/2018 | Defreitas et al. |
| 2018/0344276 A1 | 12/2018 | Defreitas et al. |
| 2019/0043456 A1 | 2/2019 | Kreeger et al. |
| 2019/0053776 A1 | 2/2019 | Ruth et al. |
| 2019/0095087 A1 | 3/2019 | Gkanatsios |
| 2019/0159741 A1 | 5/2019 | Fredenberg et al. |
| 2019/0200942 A1 | 7/2019 | Defreitas et al. |
| 2019/0325255 A1 | 10/2019 | Ren et al. |
| 2019/0392637 A1 | 12/2019 | Chen et al. |
| 2020/0012417 A1 | 1/2020 | Gkanatsios et al. |
| 2020/0022663 A1 | 1/2020 | Ren et al. |
| 2020/0258479 A1 | 8/2020 | Kreeger et al. |
| 2020/0348835 A1 | 11/2020 | Gkanatsios et al. |
| 2021/0128087 A1 | 5/2021 | Defreitas et al. |
| 2021/0204894 A1 | 7/2021 | Ren et al. |
| 2022/0005277 A1 | 1/2022 | Chen et al. |
| 2022/0013089 A1 | 1/2022 | Kreeger et al. |
| 2022/0071582 A1 | 3/2022 | Defreitas et al. |

FOREIGN PATENT DOCUMENTS

| | | |
|---|---|---|
| CN | 105451657 A | 3/2016 |
| CN | 107004283 A | 8/2017 |
| JP | 2014-128716 A | 7/2014 |
| JP | 2015-506794 A | 3/2015 |
| JP | 2017-535344 A | 11/2017 |
| JP | 2019-520885 A | 7/2019 |
| WO | 2016/078958 A1 | 5/2016 |

OTHER PUBLICATIONS

Written Opinion of the ISA issued in International Application No. PCT/JP2021/004848 on Apr. 20, 2021.
Extended European Search Report dated Jul. 20, 2023, issued in corresponding EP Patent Application No. 21771277.7.
English language translation of the following: Office action dated May 9, 2023 from the JPO in a Japanese patent application No. 2022-508132 corresponding to the instant patent application.
English language translation of the following: Office action dated Sep. 26, 2024 from the SIPO in a Chinese patent application No. 202180021255.4 corresponding to the instant patent application. This office action translation is submitted now in order to supplement the understanding of the cited references which are being disclosed in the instant Information Disclosure Statement.

* cited by examiner

IMAGE PROCESSING DEVICE, IMAGE PROCESSING METHOD, AND IMAGE PROCESSING PROGRAM

CROSS REFERENCE TO RELATED APPLICATIONS

The present application is a Continuation of PCT International Application No. PCT/JP2021/004848, filed on Feb. 9, 2021, which claims priority to Japanese Patent Application No. 2020-047342, filed on Mar. 18, 2020. Each application above is hereby expressly incorporated by reference, in its entirety, into the present application.

BACKGROUND

Technical Field

The present disclosure relates to an image processing device, an image processing method, and an image processing program.

Related Art

In recent years, image diagnosis using a radiography apparatus (called mammography) for capturing an image of a breast has attracted attention in order to promote early detection of breast cancer. Further, in the mammography, tomosynthesis imaging has been proposed which moves a radiation source, irradiates the breast with radiation at a plurality of radiation source positions to acquire a plurality of projection images, and reconstructs the plurality of acquired projection images to generate tomographic images in which desired tomographic planes have been highlighted. In the tomosynthesis imaging, the radiation source is moved in parallel to a radiation detector or is moved so as to draw a circular or elliptical arc according to the characteristics of an imaging apparatus and the required tomographic image, and imaging is performed on the breast at a plurality of radiation source positions to acquire a plurality of projection images. Then, the projection images are reconstructed using, for example, a back projection method, such as a simple back projection method or a filtered back projection method, or a sequential reconstruction method to generate tomographic images.

The tomographic images are generated in a plurality of tomographic planes of the breast, which makes it possible to separate structures that overlap each other in a depth direction in which the tomographic planes are arranged in the breast. Therefore, it is possible to find an abnormal part such as a lesion that has been difficult to detect in a two-dimensional image (hereinafter, referred to as a simple two-dimensional image) acquired by simple imaging according to the related art which irradiates an object with radiation in a predetermined direction.

In addition, a technique has been known which combines a plurality of tomographic images having different distances (positions in a height direction) from a detection surface of a radiation detector to a radiation source, which have been acquired by tomosynthesis imaging, using, for example, an addition method, an averaging method, a maximum intensity projection method, or a minimum intensity projection method to generate a pseudo two-dimensional image (hereinafter, referred to as a composite two-dimensional image) corresponding to the simple two-dimensional image (see JP2014-128716A).

In contrast, in the medical field, a computer aided diagnosis (hereinafter, referred to as CAD) system has been known which automatically detects a structure, such as an abnormal shadow, in an image and displays the detected structure so as to be highlighted. For example, the CAD is used to detect important diagnostic structures, such as a tumor, a spicula, and a calcification, from the tomographic images acquired by the tomosynthesis imaging. In addition, a method has been proposed which, in a case in which a composite two-dimensional image is generated from a plurality of tomographic images acquired by performing the tomosynthesis imaging on the breast, detects a region of interest including a structure using the CAD and combines the detected region of interest on, for example, a projection image or a two-dimensional image acquired by simple imaging to generate a composite two-dimensional image (see the specification of U.S. Pat. No. 8,983,156B). Further, a method has been proposed which averages and combines tomographic images including only the structure detected by the CAD to generate a composite two-dimensional image (see the specification of U.S. Pat. No. 9,792,703B).

However, in the composite two-dimensional image generated by the method disclosed in the specification of U.S. Pat. No. 8,983,156B, the structure of interest combined with the two-dimensional image is only the structure of interest acquired from one tomographic image. Therefore, in a case in which the structure of interest is present across a plurality of tomographic images, it is not possible to reflect a state in which the structure of interest is present in a depth direction in which the tomographic images are arranged in the composite two-dimensional image. In addition, the method disclosed in the specification of U.S. Pat. No. 9,792,703B averages the structures of interest included in a plurality of tomographic images. Therefore, for example, a fine structure of interest, such as a calcification, and a linear structure, such as spicula, included in the breast are faint and difficult to see.

SUMMARY OF THE INVENTION

The present invention has been made in view of the above circumstances, and an object of the present invention is to make it easy to see a structure of interest in a depth direction and a fine structure of interest included in an object in a composite two-dimensional image.

An image processing device according to the present disclosure comprises at least one processor. The processor is configured to detect a structure of interest from a plurality of tomographic images indicating a plurality of tomographic planes of an object, to select a tomographic image from a plurality of tomographic images according to a frequency band in a region in which a structure of interest has been detected and to generate a composite two-dimensional image using a selected tomographic image in the region in which the structure of interest has been detected and using a predetermined tomographic image in a region in which the structure of interest has not been detected.

In addition, in the image processing device according to the present disclosure, the processor may be configured to perform frequency decomposition on the plurality of tomographic images to derive a plurality of band tomographic images for each of a plurality of frequency bands, to select a band tomographic image corresponding to the tomographic image in which the structure of interest has been detected for each pixel, which corresponds to a pixel of the composite two-dimensional image, in the plurality of band tomographic images according to the frequency band, and to generate the composite two-dimensional image using the selected band tomographic image in the region in which the structure of interest has been detected.

Further, in the image processing device according to the present disclosure, the processor may be configured to select different numbers of band tomographic images corresponding to the tomographic images in which the structure of interest has been detected from the plurality of band tomographic images according to the frequency band. Furthermore, the different numbers may be 0. That is, the band tomographic image may not be selected in a certain frequency band.

Moreover, in the image processing device according to the present disclosure, the plurality of frequency bands may include a first frequency band and a second frequency band lower than the first frequency band, and the processor may be configured to select a smaller number of band tomographic images in the first frequency band than that in the second frequency band.

In addition, in the image processing device according to the present disclosure, the processor may be configured to select all of the band tomographic images including the structure of interest for each pixel, which corresponds to a pixel of the composite two-dimensional image, in the plurality of band tomographic images in the second frequency band.

Further, in the image processing device according to the present disclosure, the processor may be configured to select one band tomographic image that best represents the structure of interest for each pixel, which corresponds to a pixel of the composite two-dimensional image, in the plurality of band tomographic images in the second frequency band.

Further, in the image processing device according to the present disclosure, the processor may be configured to select one band tomographic image that best represents the structure of interest for each pixel position, which corresponds to a pixel position of the composite two-dimensional image, in the plurality of band tomographic images in the first frequency band.

Furthermore, in the image processing device according to the present disclosure, the one band tomographic image that best represents the structure of interest may be a band tomographic image having a largest structure of interest or a band tomographic image having a highest likelihood in a case in which the structure of interest is detected.

Moreover, in the image processing device according to the present disclosure, the processor may further select the band tomographic image according to a type of the structure of interest.

In addition, in the image processing device according to the present disclosure, the structure of interest may be a tumor, a spicula, and a calcification.

Further, in the image processing device according to the present disclosure, the processor may be configured to generate a composite band two-dimensional image for each frequency band using the selected band tomographic image in a pixel of the band tomographic image corresponding to the structure of interest and to perform frequency synthesis on the composite band two-dimensional images to generate the composite two-dimensional image.

Moreover, in the image processing device according to the present disclosure, the processor may be configured to generate the composite band two-dimensional image that has a pixel value of a band tomographic image determined on the basis of a predetermined priority of the structure of interest in a case in which a plurality of the band tomographic images are selected in pixels, which correspond to a pixel of the composite band two-dimensional image, in the plurality of band tomographic images.

In addition, in the image processing device according to the present disclosure, the processor may be configured to combine the plurality of tomographic images to generate a first composite two-dimensional image, to generate a composite band two-dimensional image for each frequency band using the band tomographic image selected for each type of the structure of interest in a pixel of the band tomographic image corresponding to the structure of interest, to perform frequency synthesis on the composite band two-dimensional images to generate a second composite two-dimensional image for each type of the structure of interest, and to combine the second composite two-dimensional image generated for each type of the structure of interest with the first composite two-dimensional image to generate the composite two-dimensional image.

Further, in the image processing device according to the present disclosure, the processor may be configured to replace a pixel value of the structure of interest in the first composite two-dimensional image with a pixel value of the structure of interest in the second composite two-dimensional image to combine the second composite two-dimensional image with the first composite two-dimensional image.

Furthermore, in the image processing device according to the present disclosure, the processor may be configured to generate the composite two-dimensional image having a pixel value of the second composite two-dimensional image determined on the basis of a predetermined priority of the structure of interest in a case in which a plurality of types of the structures of interest are included in corresponding pixels of the plurality of second composite two-dimensional images.

In addition, in the image processing device according to the present disclosure, the processor may be configured to combine the plurality of tomographic images to generate a first composite two-dimensional image, to extract a region of a predetermined specific type of structure of interest from the first composite two-dimensional image, to generate a composite band two-dimensional image for each frequency band, using the band tomographic image selected for each of types of structures of interest other than the specific type of structure of interest, in pixels of the band tomographic image which correspond to the other structures of interest, to perform frequency synthesis on the composite band two-dimensional images to generate a second composite two-dimensional image for each type of the other structures of interest, to combine the second composite two-dimensional images for the other structures of interest with the first composite two-dimensional image, and to combine the region of the specific type of structure of interest with the first composite two-dimensional image, with which the second composite two-dimensional images have been combined, to generate the composite two-dimensional image.

Further, in the image processing device according to the present disclosure, the specific structure of interest may be a calcification, and the other structures of interest may be a tumor and a spicula.

Further, in the image processing device according to the present disclosure, the processor may be configured to replace a pixel value of the structure of interest in the first composite two-dimensional image with a pixel value of the structure of interest in the second composite two-dimensional image to combine the second composite two-dimensional image with the first composite two-dimensional image.

Furthermore, in the image processing device according to the present disclosure, the processor may be configured to generate the composite two-dimensional image having a pixel value of the second composite two-dimensional image determined on the basis of a predetermined priority of the structure of interest in a case in which a plurality of types of the other structures of interest are included in corresponding pixels of the plurality of second composite two-dimensional images.

Moreover, in the image processing device according to the present disclosure, the processor may be configured to replace a pixel value of the structure of interest in the first composite two-dimensional image, with which the second composite two-dimensional image has been combined, with a pixel value of the region of the specific type of structure of interest to combine the region of the specific type of structure of interest with the first composite two-dimensional image with which the second composite two-dimensional image has been combined.

An image processing method according to the present disclosure comprise: detecting a structure of interest from a plurality of tomographic images indicating a plurality of tomographic planes of an object; selecting a tomographic image from the plurality of tomographic images according to a frequency band in a region in which the structure of interest has been detected; and generating a composite two-dimensional image using the selected tomographic image in the region in which the structure of interest has been detected and using a predetermined tomographic image in a region in which the structure of interest has not been detected.

In addition, a program that causes a computer to perform the image processing method according to the present disclosure may be provided.

According to the present disclosure, it is possible to easily see a structure of interest in a depth direction and a fine structure of interest included in an object in a composite two-dimensional image.

DETAILED DESCRIPTION

Figure 1:
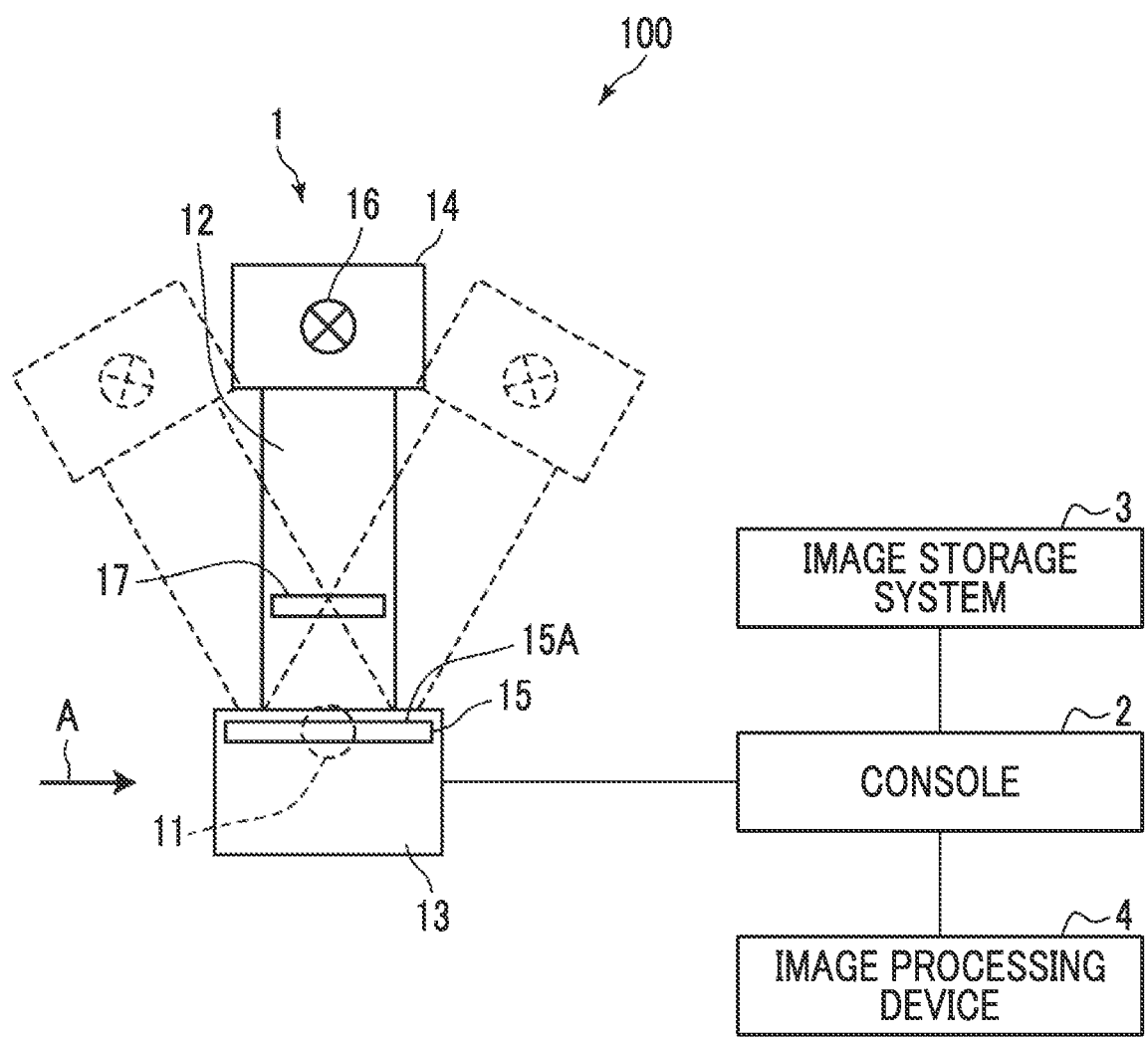
FIG. 1 is a diagram schematically illustrating a configuration of a radiography system to which an image processing device according to an embodiment of the present disclosure is applied.
Figure 2:
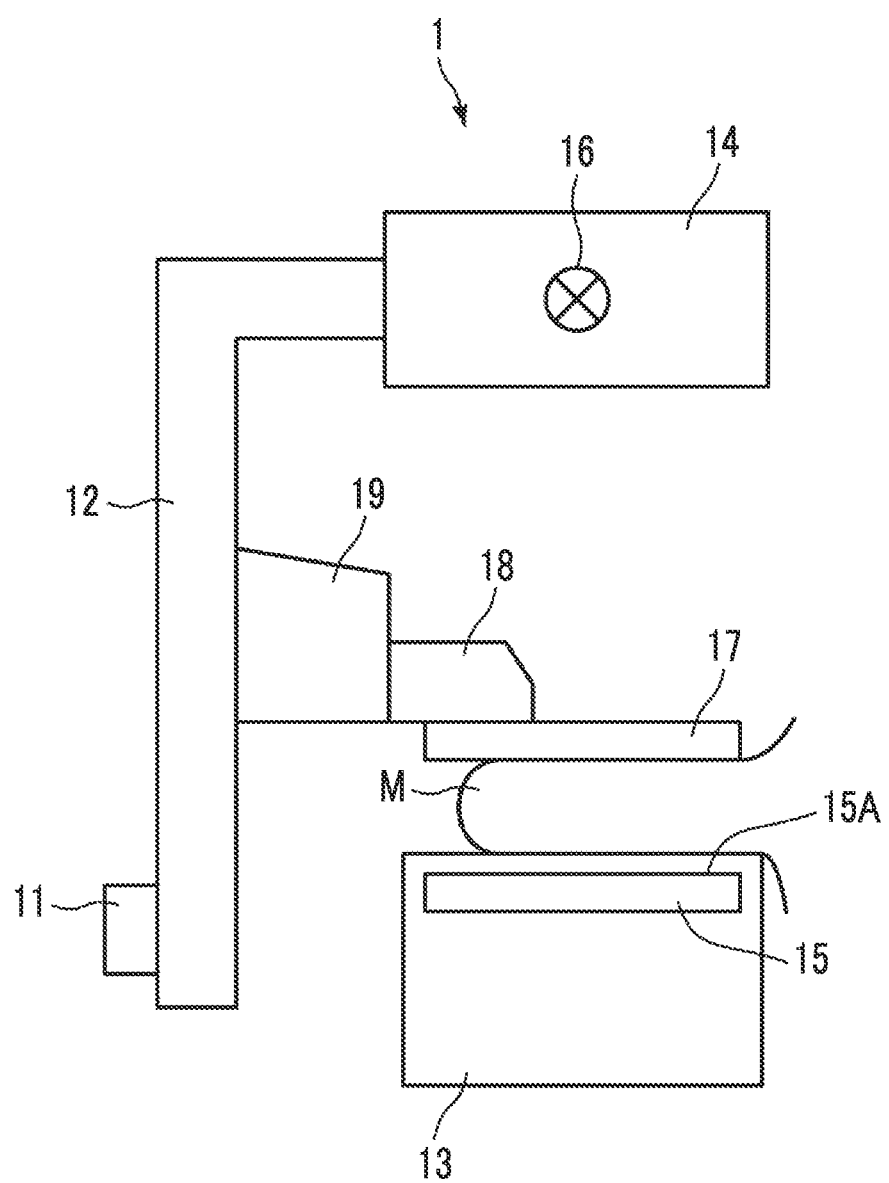
FIG. 2 is a diagram illustrating a radiography apparatus as viewed from a direction of an arrow A in FIG. 1.

Hereinafter, embodiments of the present disclosure will be described with reference to the drawings. FIG. 1 is a diagram schematically illustrating a configuration of a radiography system to which an image processing device according to an embodiment of the present disclosure is applied, and FIG. 2 is a diagram illustrating a mammography apparatus in the radiography system as viewed from a direction of an arrow A in FIG. 1. As illustrated in FIG. 1, a radiography system 100 according to this embodiment images a breast M, which is an object, at a plurality of radiation source positions and acquires a plurality of radiographic images, that is, a plurality of projection images, in order to perform tomosynthesis imaging on the breast to generate tomographic images. The radiography system 100 according to this embodiment comprises a mammography apparatus 1, a console 2, an image storage system 3, and an image processing device 4.

The mammography apparatus 1 comprises an arm portion 12 that is connected to a base (not illustrated) by a rotation shaft 11. An imaging table 13 is attached to one end of the arm portion 12, and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed, and only the radiation emitting unit 14 can be rotated.

A radiation detector 15, such as a flat panel detector, is provided in the imaging table 13. The radiation detector 15 has a detection surface 15A for radiation. In addition, for example, a circuit substrate including a charge amplifier that converts a charge signal read from the radiation detector 15 into a voltage signal, a correlated double sampling circuit that samples the voltage signal output from the charge amplifier, and an analog-digital (AD) conversion unit that converts the voltage signal into a digital signal is provided in the imaging table 13.

A radiation source 16 is accommodated in the radiation emitting unit 14. The radiation source 16 emits, for example, X-rays as the radiation. The console 2 controls the timing when the radiation source 16 emits the radiation and the radiation generation conditions of the radiation source 16, that is, the selection of target and filter materials, a tube voltage, an irradiation time, and the like.

Further, the arm portion 12 is provided with a compression plate 17 that is disposed above the imaging table 13 and presses and compresses the breast M, a support portion 18 that supports the compression plate 17, and a movement mechanism 19 that moves the support portion 18 in an up-down direction in FIGS. 1 and 2. In addition, an interval between the compression plate 17 and the imaging table 13, that is, a compression thickness is input to the console 2.

The console 2 has a function of controlling the mammography apparatus 1 using, for example, an imaging order and various kinds of information acquired from a radiology information system (RIS) (not illustrated) or the like through a network, such as a wireless communication local area network (LAN), and instructions or the like directly issued by a radiology technician or the like. Specifically, the console 2 directs the mammography apparatus 1 to perform the tomosynthesis imaging on the breast M, acquires a plurality of projection images as described below, and reconstructs the plurality of projection images to generate a plurality of tomographic images. For example, in this embodiment, a server computer is used as the console 2.

The image storage system 3 is a system that stores image data such as radiographic images and tomographic images captured by the mammography apparatus 1. The image storage system 3 extracts an image corresponding to a request from, for example, the console 2 and the image processing device 4 from the stored images and transmits the image to a device that is the source of the request. A specific example of the image storage system 3 is a picture archiving and communication system (PACS).

Figure 3:
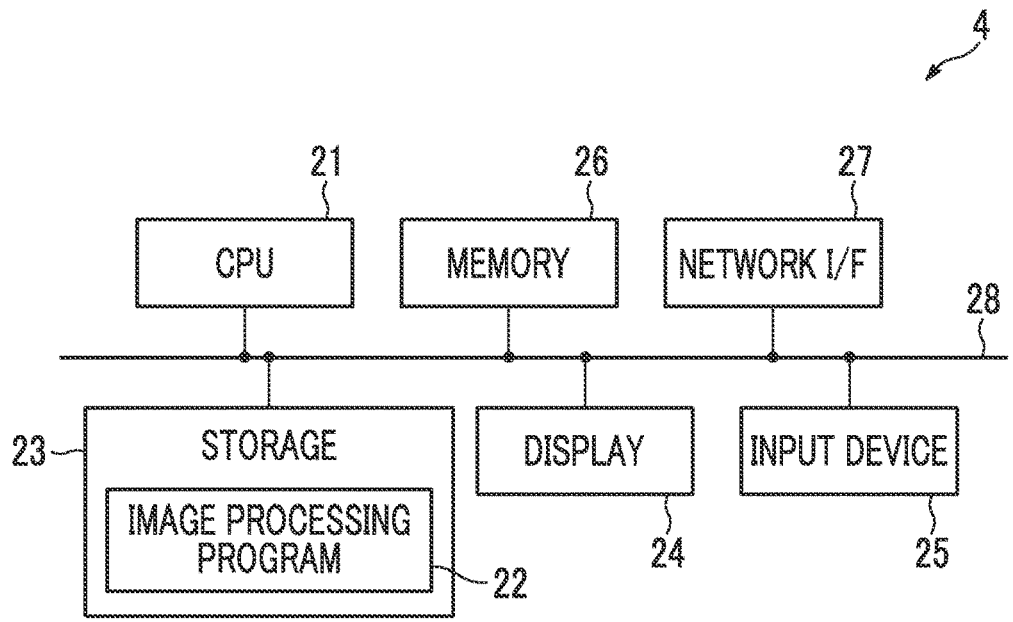
FIG. 3 is a diagram schematically illustrating a configuration of the image processing device according to a first embodiment.

Next, an image processing device according to a first embodiment will be described. Next, a hardware configuration of the image processing device according to the first embodiment will be described with reference to FIG. 3. As illustrated in FIG. 3, the image processing device 4 is a computer, such as a workstation, a server computer, or a personal computer, and comprises a central processing unit (CPU) 21, a non-volatile storage 23, and a memory 26 as a temporary storage area. In addition, the image processing device 4 comprises a display 24, such as a liquid crystal display, an input device 25, such as a keyboard and a mouse, and a network interface (I/F) 27 that is connected to a network (not illustrated). The CPU 21, the storage 23, the display 24, the input device 25, the memory 26, and the network I/F 27 are connected to a bus 28. In addition, the CPU 21 is an example of a processor according to the present disclosure.

The storage 23 is implemented by, for example, a hard disk drive (HDD), a solid state drive (SSD), and a flash memory. An image processing program 22 installed in the image processing device 4 is stored in the storage 23 as a storage medium. The CPU 21 reads out the image processing program 22 from the storage 23, expands the image processing program 22 in the memory 26, and executes the expanded image processing program 22.

In addition, the image processing program 22 is stored in a storage device of a server computer connected to the network or a network storage in a state in which it can be accessed from the outside and is downloaded and installed in the computer constituting the image processing device 4 as required. Alternatively, the programs are recorded on a recording medium, such as a digital versatile disc (DVD) or a compact disc read only memory (CD-ROM), are distributed, and are installed in the computer constituting the image processing device 4 from the recording medium.

Figure 4:
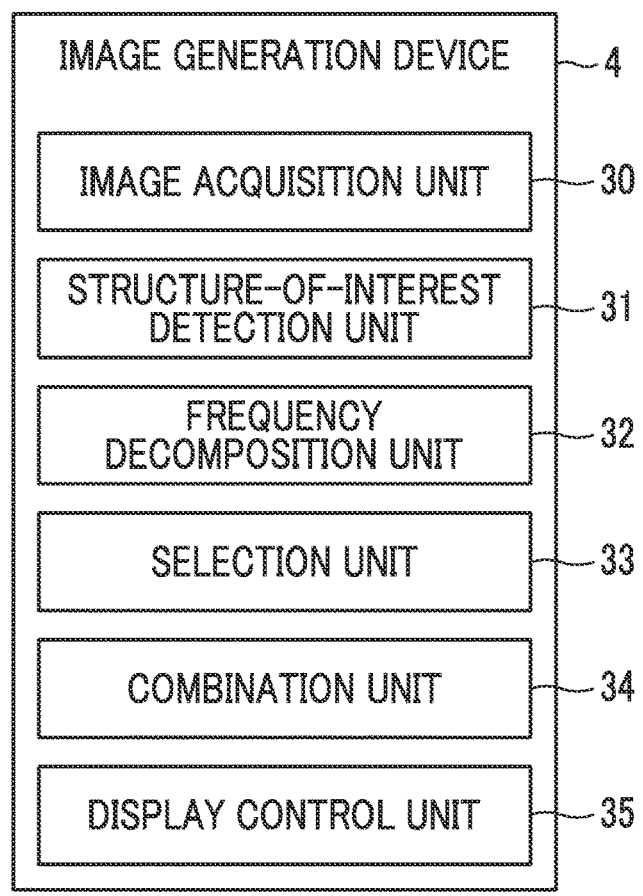
FIG. 4 is a diagram illustrating a functional configuration of the image processing device according to the first embodiment.

Next, a functional configuration of the image processing device according to the first embodiment will be described. FIG. 4 is a diagram illustrating the functional configuration of the image processing device according to the first embodiment. As illustrated in FIG. 4, the image processing device 4 comprises an image acquisition unit 30, a structure-of-interest detection unit 31, a frequency decomposition unit 32, a selection unit 33, a combination unit 34, and a display control unit 35. Then, the CPU 21 executes the image processing program 22 to function as the image acquisition unit 30, the structure-of-interest detection unit 31, the frequency decomposition unit 32, the selection unit 33, the combination unit 34, and the display control unit 35.

The image acquisition unit 30 acquires the tomographic image acquired by the imaging performed by the mammography apparatus 1 under the control of the console 2. The image acquisition unit 30 acquires the tomographic image from the console 2 or the image storage system 3 through the network I/F 27.

Here, the tomosynthesis imaging and the generation of tomographic images in the console 2 will be described. In a case in which the tomosynthesis imaging for generating tomographic images is performed, the console 2 rotates the arm portion 12 about the rotation shaft 11 to move the radiation source 16, irradiates the breast M, which is an object, with radiation at a plurality of radiation source positions caused by the movement of the radiation source 16 under predetermined imaging conditions for tomosynthesis imaging, detects the radiation transmitted through the breast M using the radiation detector 15, and acquires a plurality of projection images Gi (i=1 to n, where n is the number of radiation source positions and is, for example, 15) at the plurality of radiation source positions.

Figure 5:
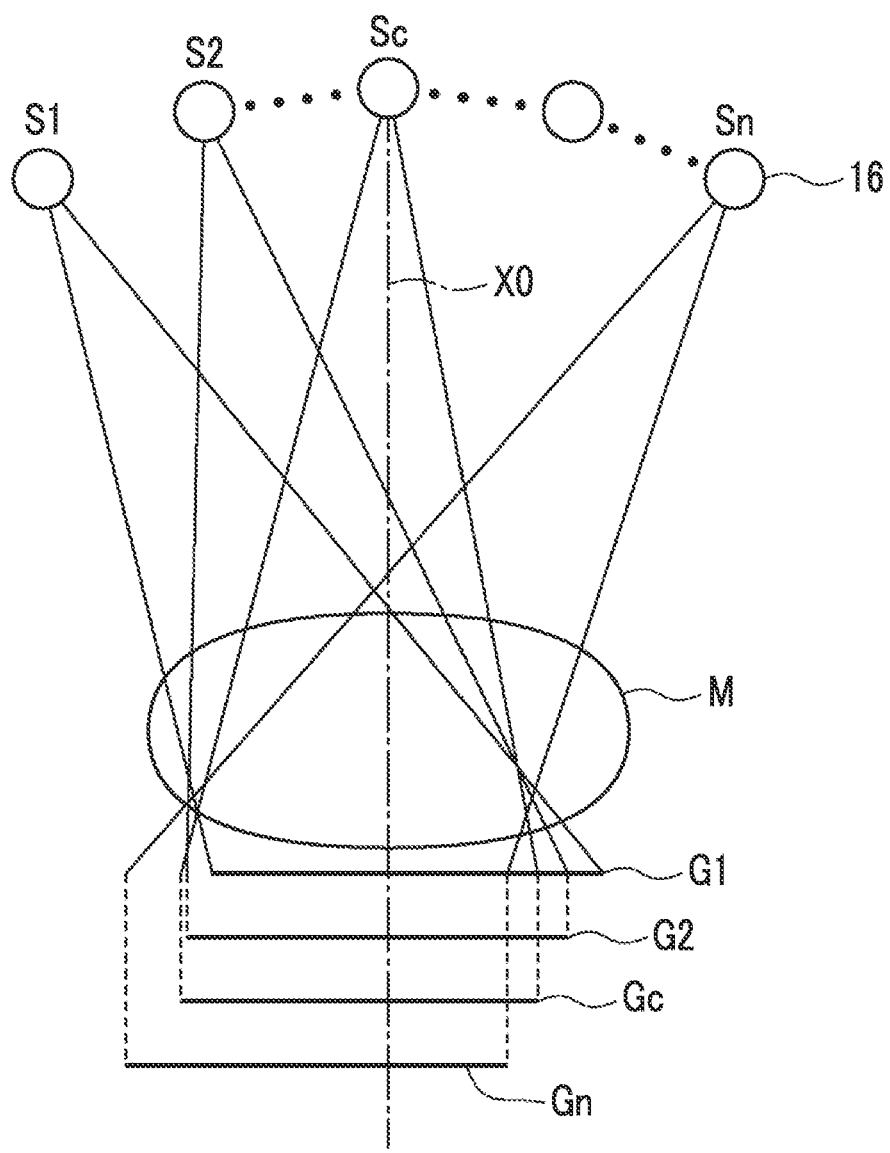
FIG. 5 is a diagram illustrating the acquisition of projection images.

FIG. 5 is a diagram illustrating the acquisition of the projection images Gi. As illustrated in FIG. 5, the radiation source 16 is moved to each of radiation source positions S1, S2, . . . , and Sn. The radiation source 16 is driven at each radiation source position to irradiate the breast M with radiation. The radiation detector 15 detects the radiation transmitted through the breast M to acquire projection images G1, G2, . . . , and Gn corresponding to the radiation source positions S1 to Sn, respectively. In addition, at each of the radiation source positions S1 to Sn, the breast M is irradiated with the same dose of radiation.

Furthermore, in FIG. 5, a radiation source position Sc is a radiation source position where an optical axis X0 of the radiation emitted from the radiation source 16 is orthogonal to the detection surface 15A of the radiation detector 15. It is assumed that the radiation source position Sc is referred to as a reference radiation source position Sc.

Figure 6:
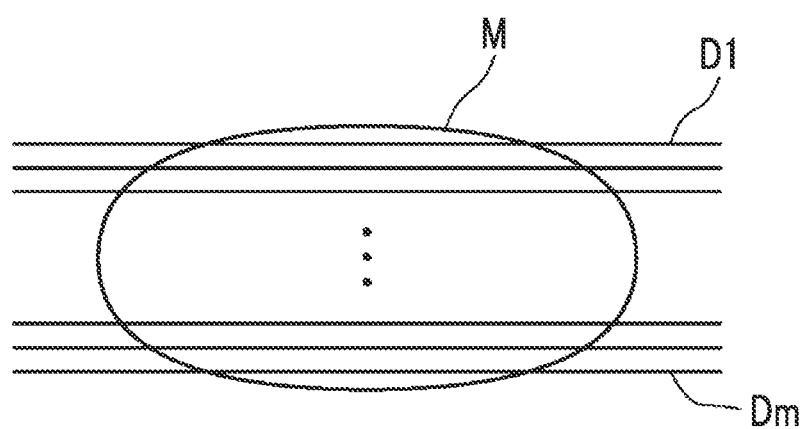
FIG. 6 is a diagram illustrating the generation of tomographic images.

Then, the console 2 reconstructs the plurality of projection images Gi to generate tomographic images in which the desired tomographic planes of the breast M have been highlighted. Specifically, the console 2 reconstructs the plurality of projection images Gi using a known back projection method, such as a simple back projection method or a filtered back projection method, to generate a plurality of tomographic images Dj (j=1 to m) in each of a plurality of tomographic planes of the breast M as illustrated in FIG. 6. In this case, a three-dimensional coordinate position in a three-dimensional space including the breast M is set, the pixel values of the corresponding pixels in the plurality of projection images Gi are reconstructed for the set three-dimensional coordinate position, and pixel values at the coordinate positions of the pixels are calculated.

The console 2 directly transmits the generated tomographic images Dj to the image processing device 4 or transmits the generated tomographic images Dj to the image storage system 3.

Figure 7:
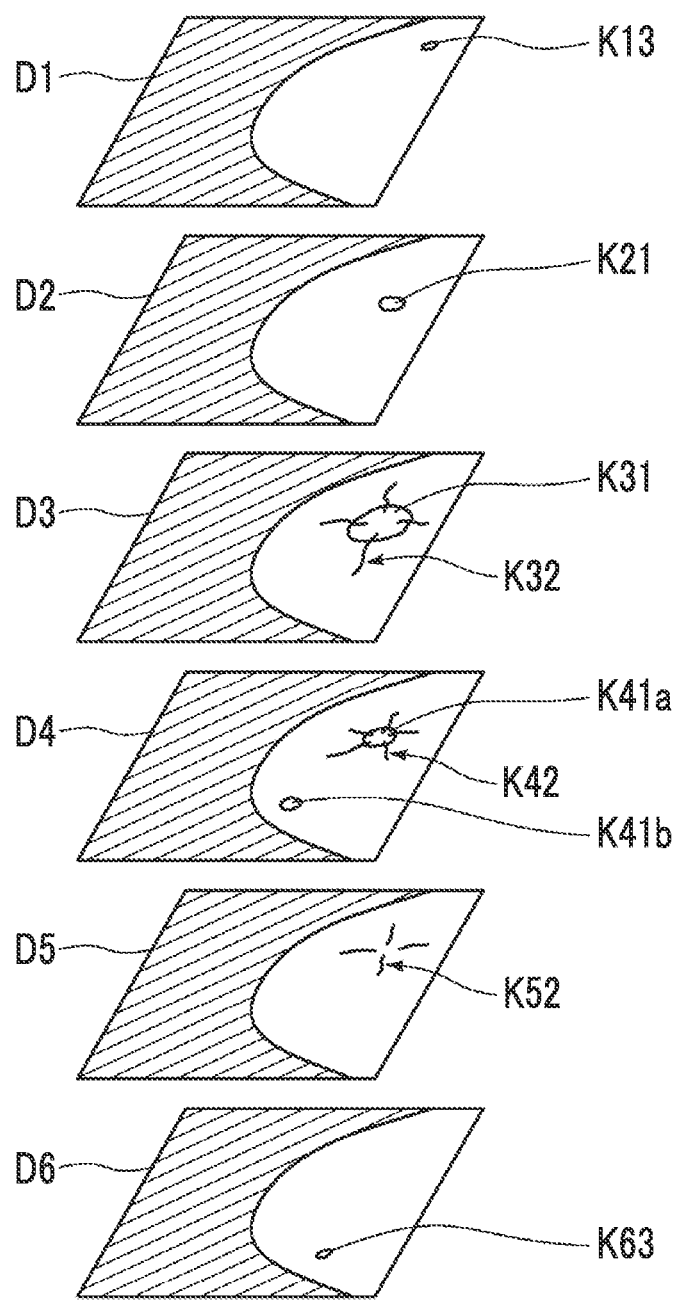
FIG. 7 is a diagram illustrating the detection of a structure of interest.

The structure-of-interest detection unit 31 detects a structure of interest from the plurality of tomographic images Dj. In this embodiment, a tumor, a spicula, and a calcification included in the breast M are detected as the structures of interest. FIG. 7 is a diagram illustrating the detection of the structures of interest. Here, the detection of the structures of interest from six tomographic images D1 to D6 will be described. As illustrated in FIG. 7, the tomographic image D1 includes a calcification K13. The tomographic image D2 includes a tumor K21. The tomographic image D3 includes a tumor K31 which is contiguous with the tumor K21 in the tomographic image D2 in the breast M and a spicula K32. The tomographic image D4 includes a tumor K41*a* which is contiguous with the tumor K21 in the tomographic image D2 and the tumor K31 in the tomographic image D3 in the breast M, a tumor K41*b* which is present only in the tomographic image D4, and a spicula K42. The tomographic image D5 includes a spicula K52. The tomographic image D6 includes a calcification K63.

The structure-of-interest detection unit 31 detects the structure of interest from the tomographic images Dj using a known computer-aided diagnosis (that is, CAD) algorithm. In the CAD algorithm, the probability (likelihood) that the pixel in the tomographic images Dj will be the structure of interest is derived, and a pixel having a probability equal to or greater than a predetermined threshold value is detected as the structure of interest. In addition, the CAD algorithm is prepared for each type of structure of interest. In this embodiment, a CAD algorithm for detecting a tumor, a CAD algorithm for detecting a spicula, and a CAD algorithm for detecting a calcification are prepared.

Further, the detection of the structure of interest is not limited to the method using the CAD. The structure of interest may be detected from the tomographic images Dj by a filtering process using a filter for detecting the structure of interest, a detection model which has been subjected to machine learning by deep learning and the like to detect the structure of interest, and the like.

Figure 8:
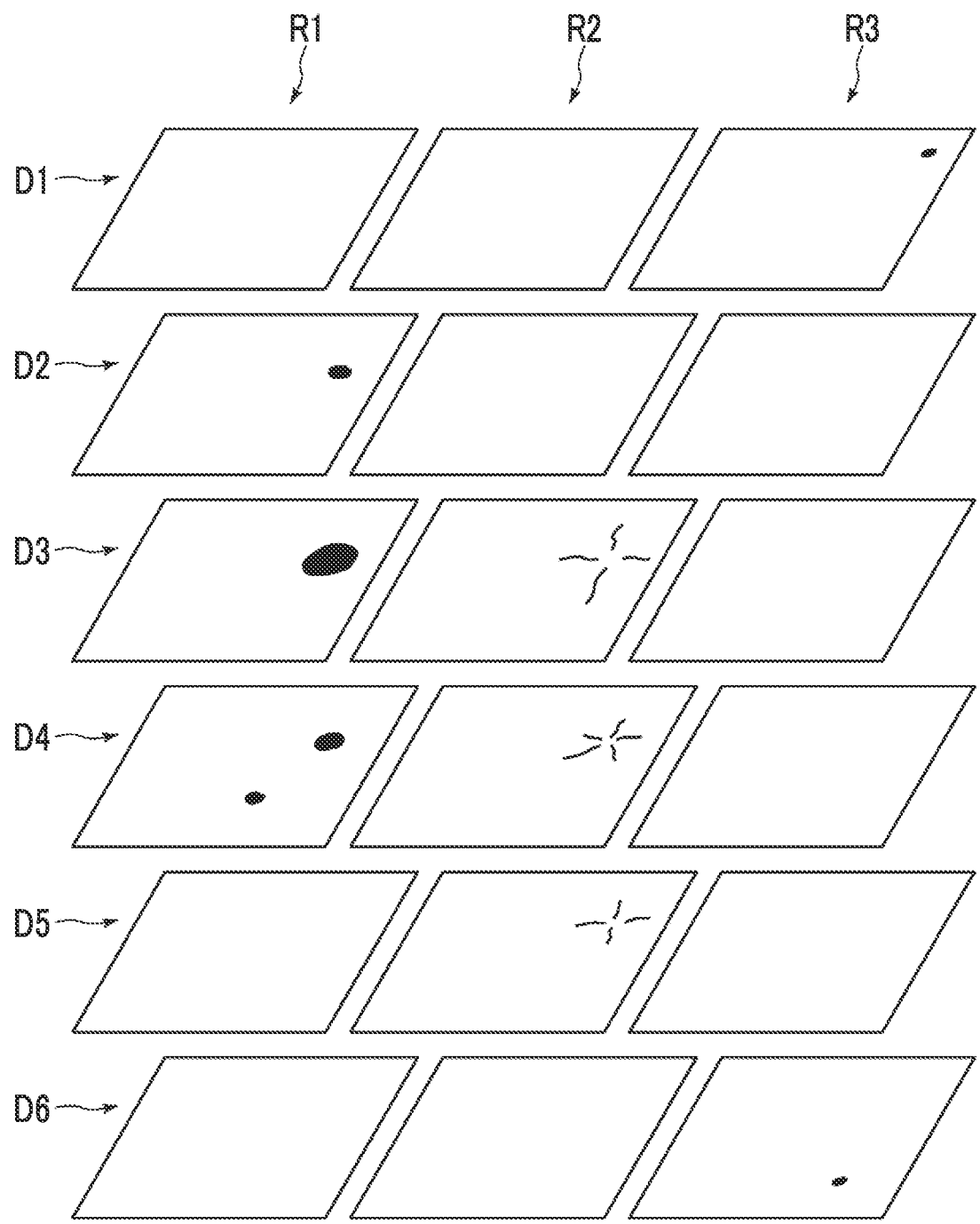
FIG. 8 is a diagram illustrating a detection result of the structure of interest.

The structure-of-interest detection unit 31 detects the tumor, the spicula, and the calcification as the structures of interest from the tomographic images D1 to D6 illustrated in FIG. 7 and derives a detection result R1 of the tumor, a detection result R2 of the spicula, and a detection result R3 of the calcification as illustrated in FIG. 8. In the detection result R1 of the tumor, the tumor is detected in the tomographic images D2 to D4. In the detection result R2 of the spicula, the spicula is detected in the tomographic images D3 to D5. In the detection result R3 of the calcification, the calcification is detected in the tomographic images D1 and D6.

The frequency decomposition unit 32 performs frequency decomposition on each of the plurality of tomographic images Dj to derive a plurality of band tomographic images indicating frequency components in each of a plurality of frequency bands for each of the plurality of tomographic images Dj. In addition, any known methods, such as wavelet transform and Fourier transform, can be used as a frequency decomposition method, in addition to a method for performing multiple resolution transformation on a radiographic image. Further, the number of bands obtained by frequency decomposition may be two or more. Furthermore, in this embodiment, a low frequency band, a medium frequency band, and a high frequency band are described as the frequency bands. However, for the frequency components included in the band tomographic images, the high frequency band includes the largest number of frequency components, followed by the medium frequency band and the low frequency band in this order. Moreover, in a case in which the frequency is decomposed into four or more frequency bands, the low frequency band, the medium frequency band, and the high frequency band can be set in any manner. In addition, in a case in which the number of bands obtained by the frequency decomposition is two, it is assumed that the lower frequency band is referred to as a medium-low frequency band and the higher frequency band is referred to as a high frequency band. Further, even in a case in which the number of bands obtained by the frequency decomposition is four or more, it is assumed that the low frequency band and the medium frequency band may be collectively referred to as the medium-low frequency band.

Figure 9:
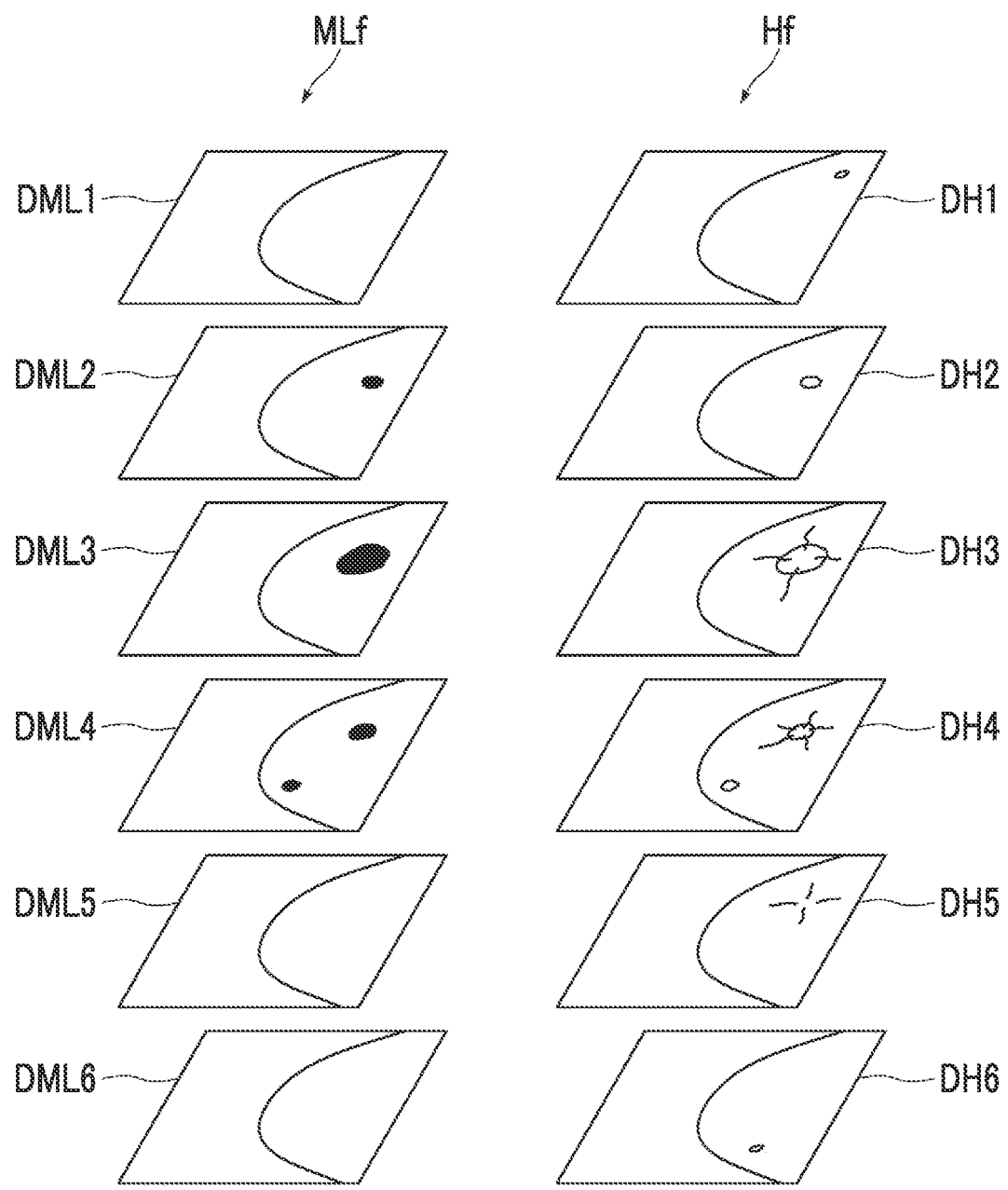
FIG. 9 is a diagram illustrating band tomographic images.

FIG. 9 is a diagram illustrating band tomographic images. In addition, in FIG. 9, for simplicity of description, only a medium-low frequency band MLf and a high frequency band Hf are illustrated as a plurality of frequency bands. Further, the high frequency band Hf corresponds to a first frequency band according to the present disclosure, and the medium-low frequency band MLf corresponds to a second frequency band according to the present disclosure. Furthermore, it is assumed that the band tomographic images in the medium-low frequency band MLf are represented by DML1 to DML6 and the band tomographic images in the high frequency band Hf are represented by DH1 to DH6. The band tomographic images DML1 to DML6 in the medium-low frequency band MLf include only the tumor having a relatively large structure among the tumor, the spicula, and the calcification included in the tomographic images D1 to D6. The band tomographic images DH1 to DH6 in the high frequency band include the spicula and the calcification having a fine structure and the tumor having a fine structure.

In the region in which the structure of interest has been detected, the selection unit 33 selects a tomographic image from the plurality of tomographic images Dj according to the type of the structure of interest and the frequency band. Specifically, in the first embodiment, the selection unit 33 selects a band tomographic image corresponding to the tomographic image, in which the structure of interest has been detected, from the plurality of band tomographic images for each pixel, which corresponds to the pixels of a composite two-dimensional image CG0 which will be described below, in the plurality of band tomographic images according to the type of the structure of interest and the frequency band. In addition, in a case in which a band tomographic image is selected, the selection unit 33 associates the position of the structure of interest in the tomographic images Dj with the positions of the band tomographic images DMLj and DHj for each type of structure of interest detected by the structure-of-interest detection unit 31.

Figure 10:
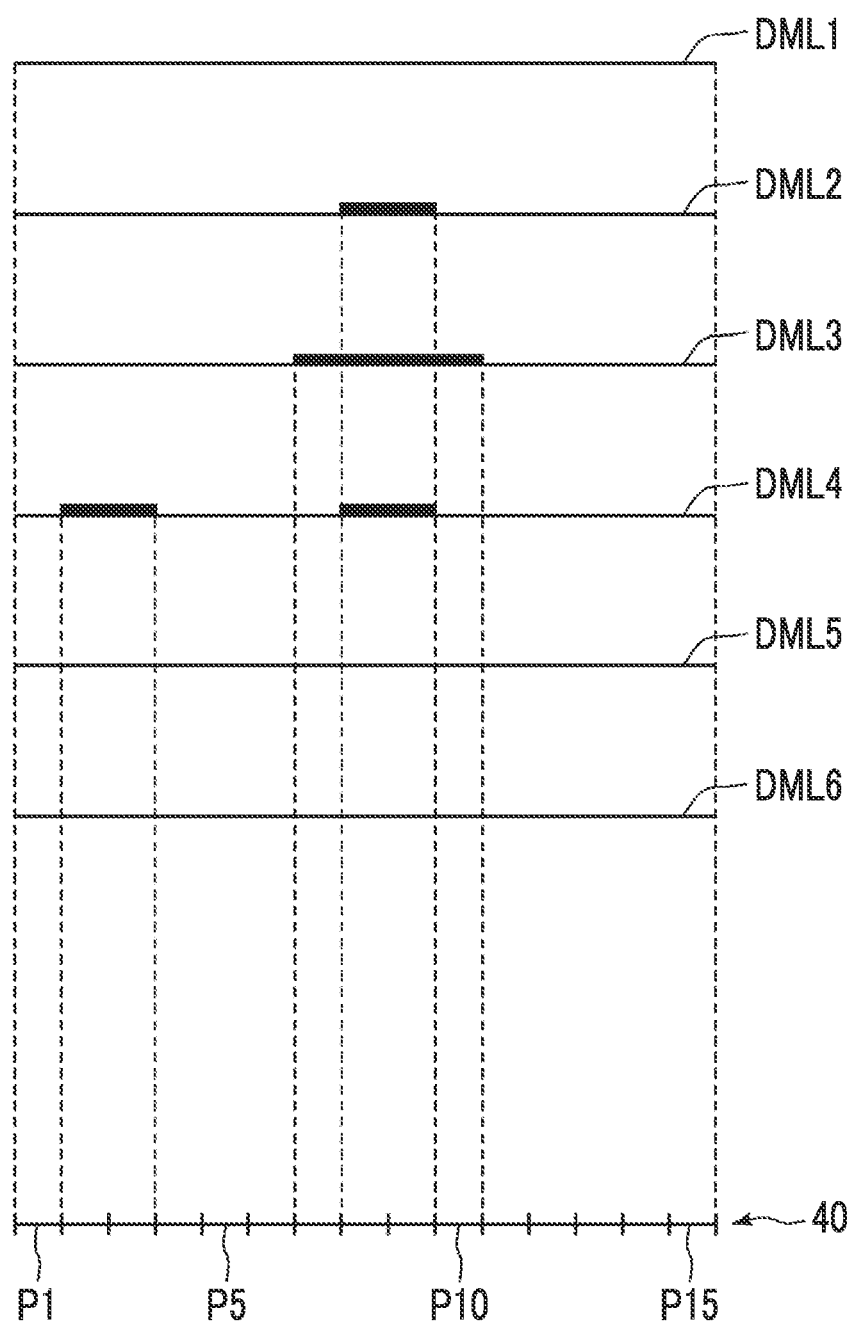
FIG. 10 is a diagram illustrating the selection of a band tomographic image for a tumor in a medium-low frequency band.
Figure 11:
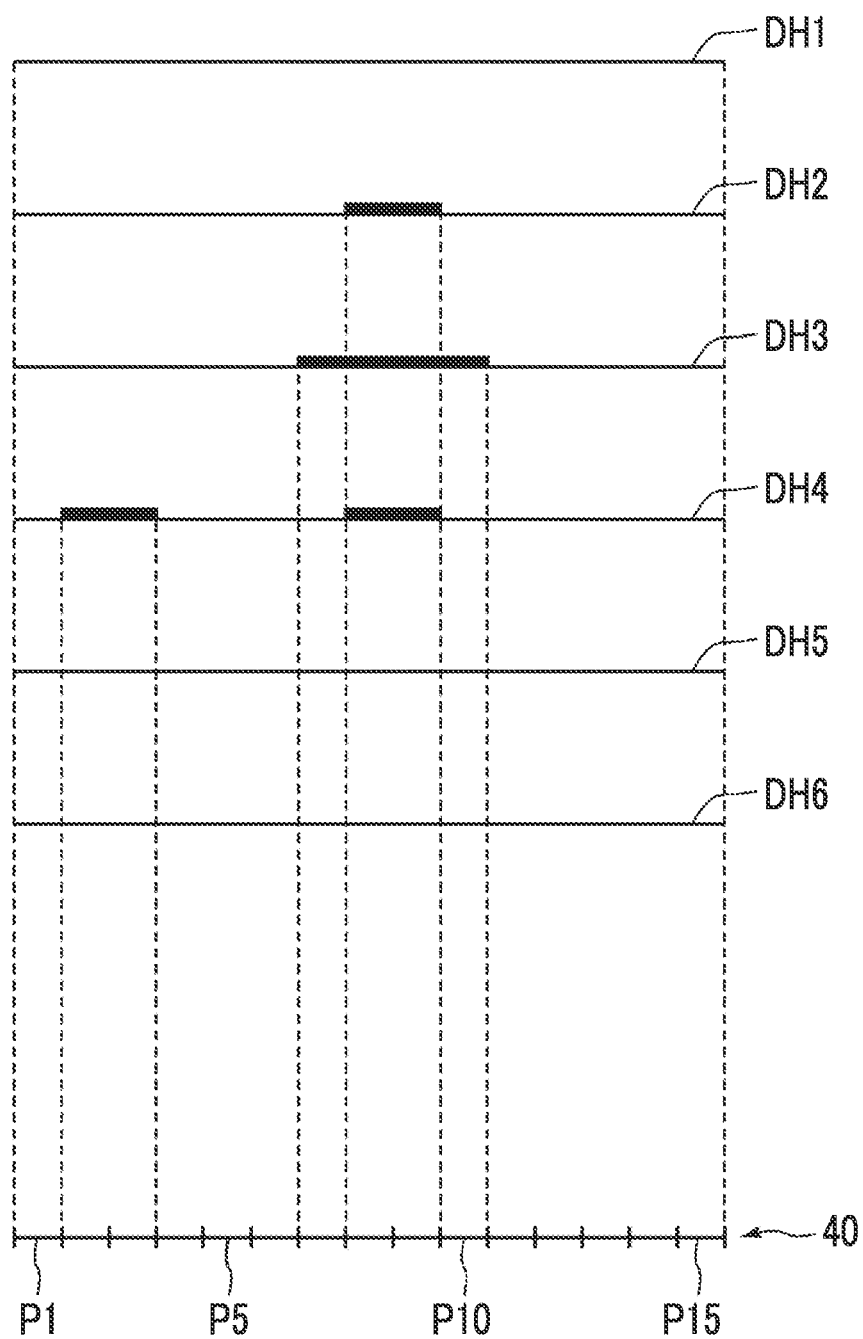
FIG. 11 is a diagram illustrating the selection of the band tomographic image for the tumor in a high frequency band.
Figure 12:
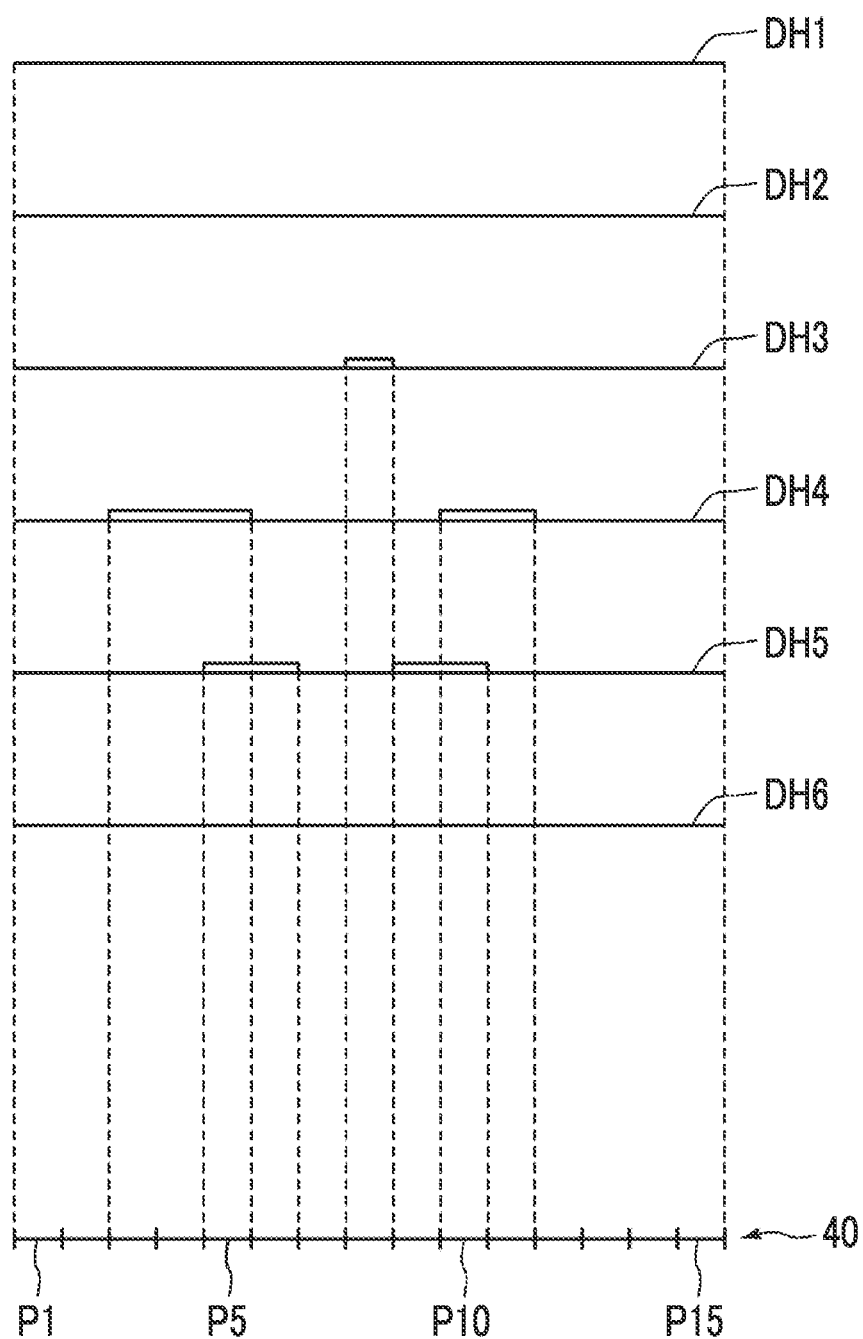
FIG. 12 is a diagram illustrating the selection of a band tomographic image for a spicula in the high frequency band.
Figure 13:
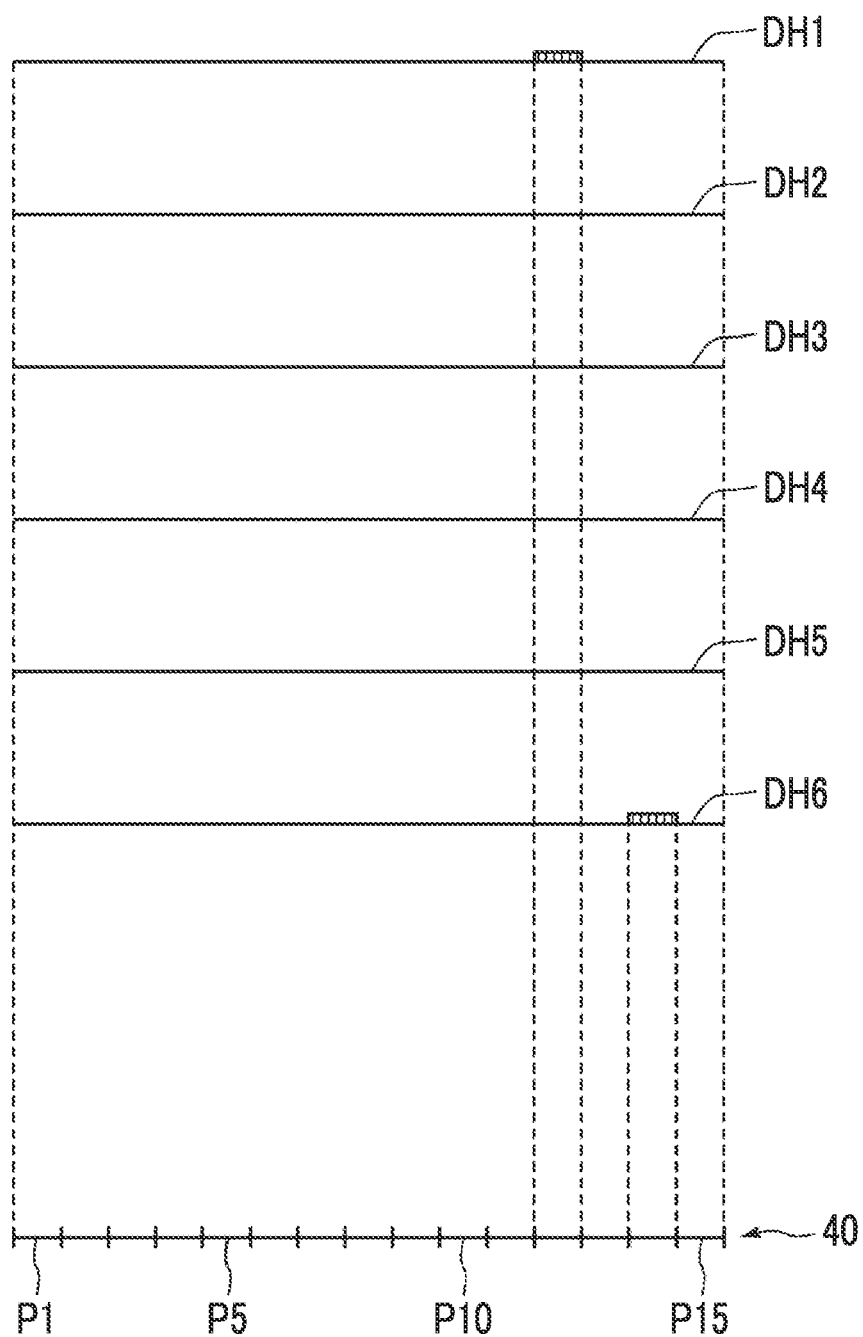
FIG. 13 is a diagram illustrating the selection of a band tomographic image for a calcification in the high frequency band.

FIG. 10 is a diagram illustrating the selection of the band tomographic image for the tumor in the medium-low frequency band. FIG. 11 is a diagram illustrating the selection of the band tomographic image for the tumor in the high frequency band. FIG. 12 is a diagram illustrating the selection of the band tomographic image for the spicula in the high frequency band. FIG. 13 is a diagram illustrating the selection of the band tomographic image for the calcification in the high frequency band. In addition, FIGS. 10 to 13 schematically illustrate the tomographic images one-dimensionally. Further, in FIGS. 10 to 13, an index 40 for showing a correspondence relationship between the pixels of the band tomographic image and the pixels of the composite two-dimensional image CG0 is one-dimensionally illustrated. Furthermore, in the band tomographic image including the structure of interest, the pixel of the detected structure of interest is illustrated to be thicker than the pixels other than the structure of interest. Moreover, in FIGS. 10 and 11, the pixel of the tumor is painted black. In FIG. 12, the pixel of the spicula is painted white. In FIG. 13, the pixel of the calcification is vertically hatched. In addition, in the index 40, 15 pixels P1 to P15 corresponding to the pixels of the composite two-dimensional image CG0 are illustrated. Further, in the index 40, only the pixels P1, P5, P10, and P15 are denoted by reference numerals. Furthermore, in the following description, the same figures as FIGS. 10 to 13 are illustrated in the same manner as FIGS. 10 to 13.

First, the selection of the band tomographic image for the tumor will be described. For the tumor, the selection unit 33 selects all of the band tomographic images including the tumor for each pixel, which corresponds to the pixels of the composite two-dimensional image CG0, in a plurality of band tomographic images in the medium-low frequency band MLf. As illustrated in FIG. 10, in the pixels P1, P4 to P6, and P11 to P15 of the band tomographic images DMLj in the medium-low frequency band MLf, no tumor is detected in all of the band tomographic images DMLj. Therefore, for the tumor, the selection unit 33 does not select any band tomographic image for the pixels P1, P4 to P6, and P11 to P15. Further, in the pixels P2 and P3, the tumor is detected only in the band tomographic image DML4. Therefore, the selection unit 33 selects the band tomographic image DML4 for the pixels P2 and P3. In the pixels P7 and P10, the tumor is detected only in the band tomographic image DML3. Therefore, the selection unit 33 selects the band tomographic image DML3 for the pixels P7 and P10. Furthermore, in the pixels P8 and P9, the tumor is detected in the band tomographic images DML2 to DML4. Therefore, the selection unit 33 selects all of the band tomographic images DML2 to DML4 in which the tumor has been detected for the pixels P8 and P9.

Meanwhile, in the high frequency band Hf, the selection unit 33 selects one band tomographic image that best represents the tumor for each pixel, which corresponds to the pixels of the composite two-dimensional image CG0, in the plurality of band tomographic images. As illustrated in FIG. 11, in the pixels P1, P4 to P6, and P11 to P15 of the band tomographic images DHj in the high frequency band Hf, no tumor is detected in all of the band tomographic images DHj. Therefore, for the tumor, the selection unit 33 does not select any band tomographic image for the pixels P1, P4 to P6, and P11 to P15. Further, in the pixels P2 and P3, the tumor is detected only in the band tomographic image DH4. Therefore, the selection unit 33 selects the band tomographic image DH4 for the pixels P2 and P3. In the pixels P7 and P10, the tumor is detected only in the band tomographic image DH3. Therefore, the selection unit 33 selects the band tomographic image DH3 for the pixels P7 and P10. Furthermore, in the pixels P8 and P9, the tumor is detected in the band tomographic images DH2 to DH4. Here, among the tumors detected in the band tomographic images DH2 to DH4, the tumor detected in the band tomographic images DH3 is the largest, and the band tomographic image DH3 among the band tomographic images DH2 to DH4 best represents the tumor. Therefore, the selection unit 33 selects the band tomographic image DH3 for the pixels P8 and P9. Moreover, instead of the largest tumor, a band tomographic image including the tumor having the highest probability (likelihood) derived by the structure-of-interest detection unit 31 at the time of detection may be selected.

Next, the selection of the band tomographic image for the spicula will be described. The structure of the spicula is included only in the band tomographic image DHj in the high frequency band Hf. Therefore, the selection unit 33 selects one band tomographic image that best represents the spicula for each pixel, which corresponds to the pixels of the composite two-dimensional image CG0, in the plurality of band tomographic images only in the high frequency band Hf As illustrated in FIG. 12, in the pixels P1, P2, P7, and P12 to P15, no spicula is detected in all of the band tomographic images DHj. Therefore, for the spicula, the selection unit 33 does not select any band tomographic image DHj for the pixels P1, P2, P7, and P12 to P15. In addition, in the pixels P3, P4, and P11, the spicula is detected only in the band tomographic image DH4. Therefore, the selection unit 33 selects the band tomographic image DH4 for the pixels P3, P4, and P11. Further, in the pixels P5 and P10, the spicula is detected in the band tomographic images DH4 and DH5. Here, of the spiculae detected in the band tomographic images DH4 and DH5, the spicula detected in the band tomographic images DH4 is the largest, and the band tomographic image DH4 of the band tomographic images DH4 and DH5 best represents the spicula. Therefore, the selection unit 33 selects the band tomographic image DH4 for the pixels P5 and P10. In addition, instead of the largest spicula, a tomographic image including the spicula having the highest probability (likelihood) derived by the structure-of-interest detection unit 31 at the time of detection may be selected.

In the pixels P6 and P9, the spicula is detected only in the band tomographic image DH5. Therefore, the selection unit 33 selects the band tomographic image DH5 for the pixels P6 and P9. Further, in the pixel P8, the spicula is detected in the band tomographic image DH3. Therefore, the selection unit 33 selects the band tomographic image DH3 for the pixel P8.

Next, the selection of the band tomographic image for the calcification will be described. The structure of the calcification is included only in the band tomographic image DHj in the high frequency band Hf. Therefore, the selection unit 33 selects one band tomographic image that best represents the calcification for each pixel, which corresponds to the pixels of the composite two-dimensional image CG0, in the plurality of band tomographic images only in the high frequency band Hf. As illustrated in FIG. 13, in the pixels P1 to P11, P13, and P15, the calcification is not detected in all of the band tomographic images DHj. Therefore, for the calcification, the selection unit 33 does not select any band tomographic image for the pixels P1 to P11, P13, and P15. In addition, in the pixel P12, the calcification is detected only in the band tomographic image DH1. Therefore, the selection unit 33 selects the band tomographic image DH1 for the pixel P12. In the pixel P14, the calcification is detected only in the band tomographic image DH6. Therefore, the selection unit 33 selects the band tomographic image DH6 for the pixel P14.

Figure 14:
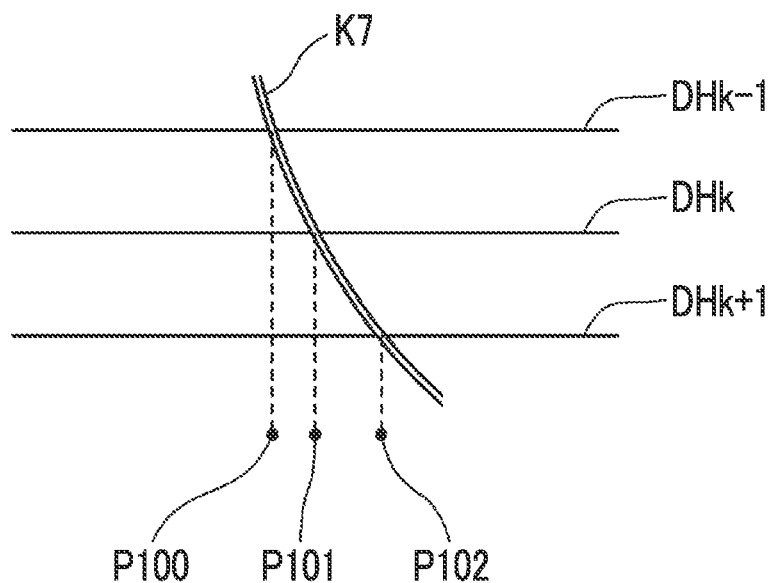
FIG. 14 is a diagram illustrating a spicula extending across a plurality of tomographic images.

Further, for the spicula, as illustrated in FIG. 14, in some cases, one spicula K7 spreads two-dimensionally in a direction orthogonal to the tomographic plane and is present across a plurality of band tomographic images DHk−1, DHk, and DHk+1. In this case, the spicula is detected in a pixel P100 for the band tomographic image DHk−1, is detected in a pixel P101 for the band tomographic image DHk, and is detected in a pixel P102 for the band tomographic image DHk+1. Therefore, in a case in which the spicula K7 is present in the breast M as illustrated in FIG. 14 and the band tomographic image DHk illustrated in FIG. 14 is selected, a plurality of band tomographic images DHk−1 and DHk+1, which are above and below the band tomographic image DHk and to which the spicula K7 included in the band tomographic image DHk is connected, are also selected.

Figure 15:
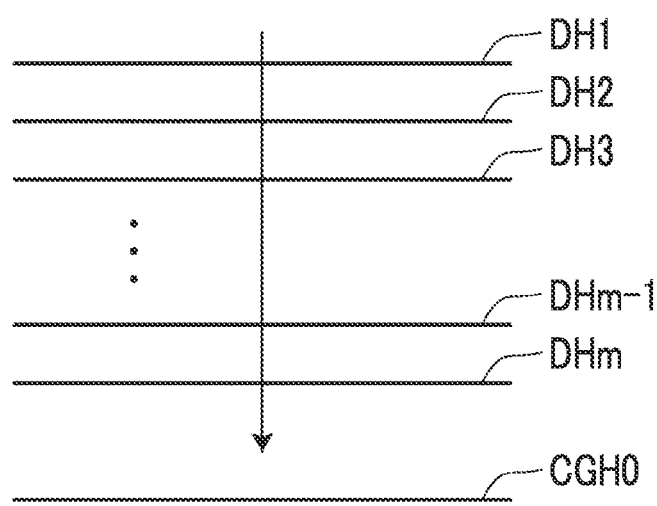
FIG. 15 is a diagram illustrating the generation of a composite band two-dimensional image.

The combination unit 34 generates a composite two-dimensional image using the band tomographic images selected for each type of structure of interest by the selection unit 33 according to the frequency band. Specifically, the combination unit 34 generates a composite band two-dimensional image for each frequency band using the selected band tomographic images in the pixels of the band tomographic images, which correspond to the structure of interest, and performs frequency synthesis on the composite band two-dimensional images to generate a composite two-dimensional image. The composite two-dimensional image is a pseudo two-dimensional image corresponding to a simple two-dimensional image that is captured by irradiating the breast M with radiation emitted at the reference radiation source position Sc. In this embodiment, as illustrated in FIG. 15, the combination unit 34 generates a composite band two-dimensional image CGH0 by combining the pixel values of the corresponding pixels in each of the band tomographic images DHj along a viewing direction from the reference radiation source position Sc to the radiation detector 15, that is, along the optical axis X0 illustrated in FIG. 5 in a state in which the plurality of band tomographic images (only DHj is illustrated in FIG. 15) are stacked. Hereinafter, the generation of the composite band two-dimensional image or the composite two-dimensional image will be described.

Figure 16:
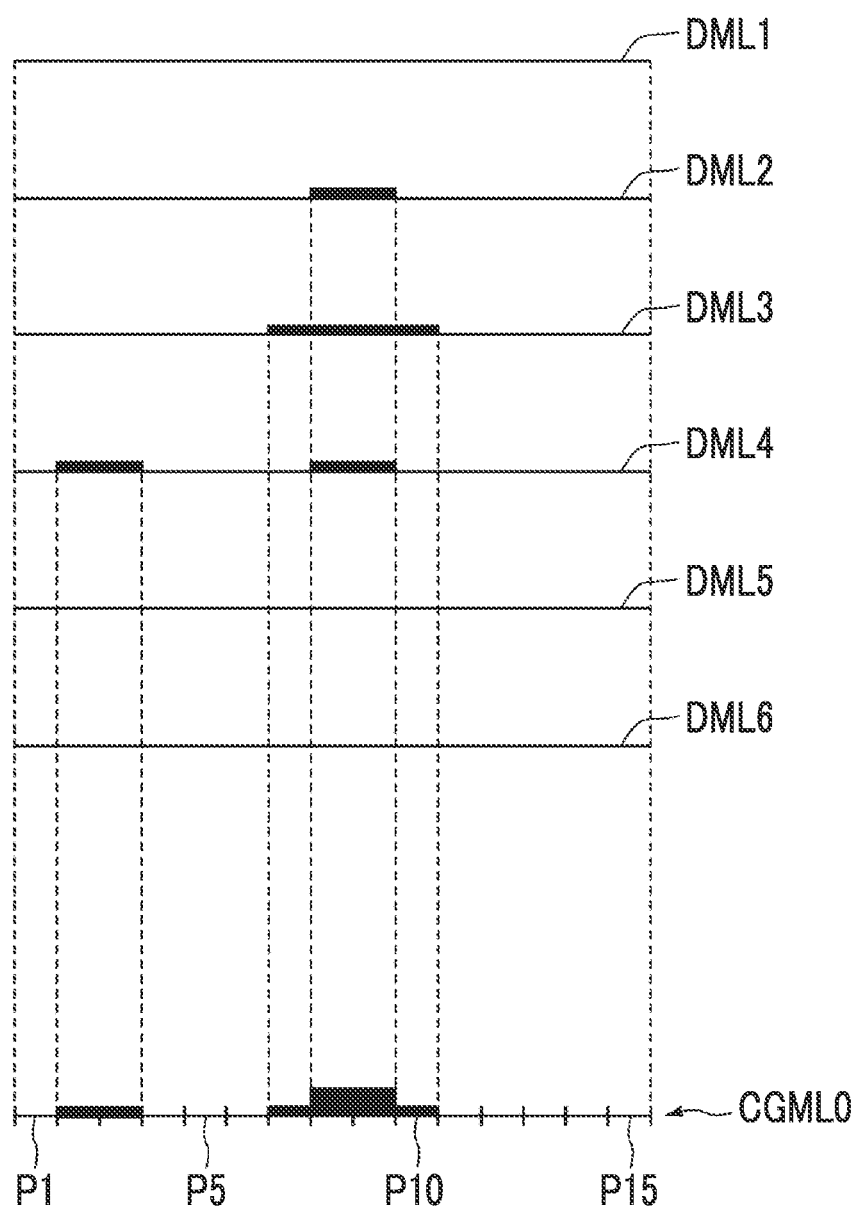
FIG. 16 is a diagram illustrating the generation of the composite band two-dimensional image in the medium-low frequency band.

FIG. 16 is a diagram illustrating the generation of the composite band two-dimensional image in the medium-low frequency band MLf. As illustrated in FIG. 16, for the pixels P1, P4 to P6, and P11 to P15 in which no tumor is detected, the combination unit 34 derives the added average value of the pixel values of all of the band tomographic images DML1 to DML6 and sets the added average value as the pixel values of the pixels P1, P4 to P6, and P11 to P15 of the composite band two-dimensional image CGML0 in the medium-low frequency band MLf. In this case, all of the band tomographic images are predetermined tomographic images according to the present disclosure. Since the band tomographic image DML4 in which the tumor has been detected is selected for the pixels P2 and P3, the combination unit 34 sets the pixel values of the pixels P2 and P3 of the band tomographic image DML4 as the pixel values of the pixels P2 and P3 of the composite band two-dimensional image CGML0. Since the band tomographic image DML3 is selected for the pixels P7 and P10 of the band tomographic image DMLj, the combination unit 34 sets the pixel values of the pixels P7 and P10 of the band tomographic image DML3 as the pixel values of the pixels P7 and P10 of the composite band two-dimensional image CGML0. Since the band tomographic images DML2 to DML4 are selected for the pixels P8 and P9 of the band tomographic images DMLj, the combination unit 34 sets the added value of the pixel values of the pixels P8 and P9 of the band tomographic images DML2 to DML4 as the pixel values of the pixels P8 and P9 of the composite band two-dimensional image CGML0. In addition, a weighted added value, a weighted average value, or the like may be used instead of the added value. In this case, a weight for the band tomographic image DML3 may be larger than those for the band tomographic images DML2 and DML4.

Figure 17:
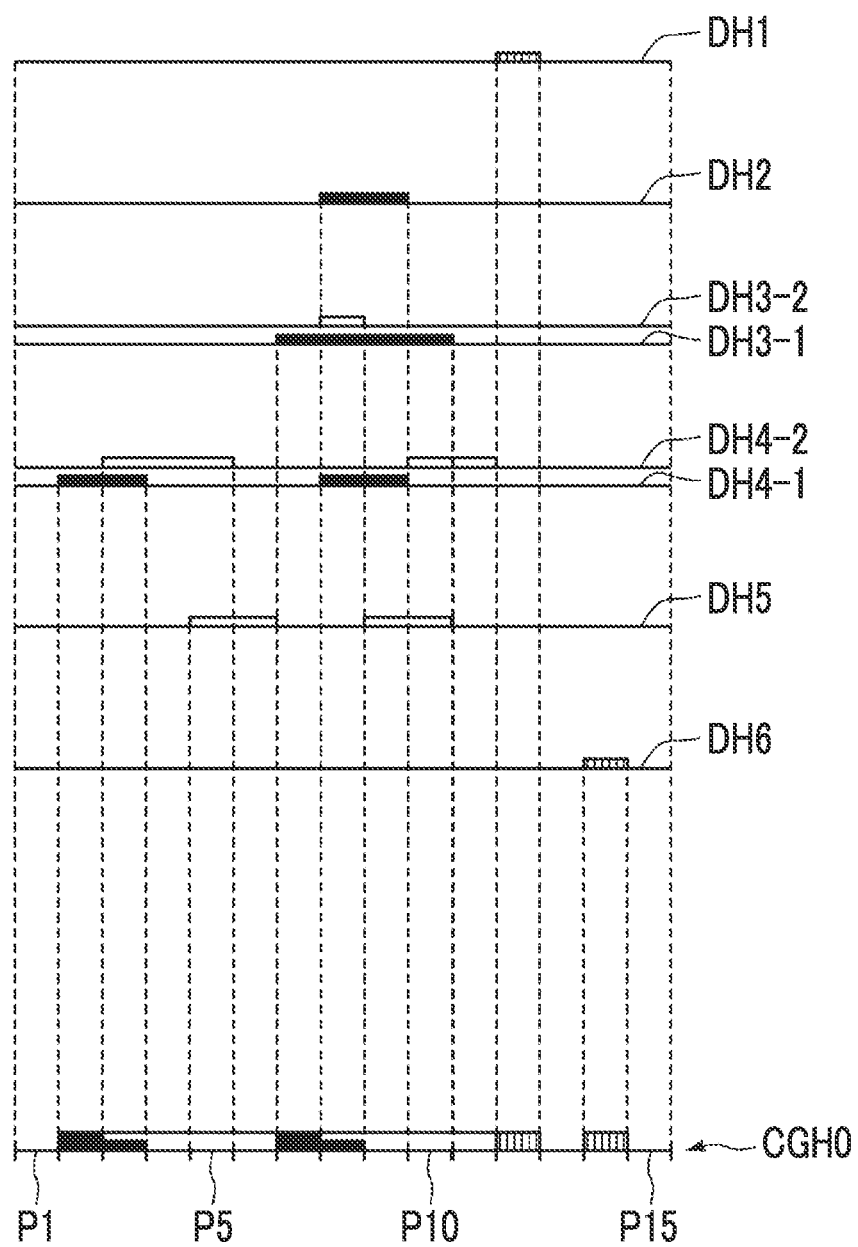
FIG. 17 is a diagram illustrating the generation of the composite band two-dimensional image in the high frequency band.

FIG. 17 is a diagram illustrating the generation of the composite band two-dimensional image in the high frequency band Hf. In addition, the band tomographic images DH3 and DH4 include both the tumor and the spicula. Therefore, in FIG. 17, band tomographic images DH3-1 and DH4-1 including the detection result of only the tumor and band tomographic images DH3-2 and DH4-2 including the detection result of only the spicula are virtually illustrated side by side. Further, in the following description, the same figures as FIG. 17 are illustrated in the same manner as FIG. 17.

As illustrated in FIG. 17, for the pixels P1, P13, and P15 in which none of the structures of interest of the tumor, the spicula, and the calcification are detected, the combination unit 34 derives the added average value of the pixel values of all of the band tomographic images DH1 to DH6 and sets the added average value as the pixel values of the pixels P1, P13, and P15 of the composite band two-dimensional image CGH0 in the high frequency band Hf. Since the band tomographic image DH4 in which the tumor has been detected is selected for the pixel P2, the combination unit 34 sets the pixel value of the pixel P2 of the band tomographic image DH4 as the pixel value of the pixel P2 of the composite band two-dimensional image CGH0. Since the band tomographic image DH4 in which the tumor and the spicula have been detected is selected for the pixel P3, the combination unit 34 sets the pixel value of the pixel P3 of the band tomographic image DH4 as the pixel value of the pixel P3 of the composite band two-dimensional image CGH0. Since the band tomographic image DH4 in which the spicula has been detected is selected for the pixels P4 and P5, the combination unit 34 sets the pixel values of the pixels P4 and P5 of the band tomographic image DH4 as the pixel values of the pixels P4 and P5 of the composite band two-dimensional image CGH0.

Since the band tomographic image DH5 in which the spicula has been detected is selected for the pixel P6, the combination unit 34 sets the pixel value of the pixel P6 of the band tomographic image DH5 as the pixel value of the pixel P6 of the composite band two-dimensional image CGH0. Since the band tomographic image DH3 in which the tumor has been detected is selected for the pixel P7, the combination unit 34 sets the pixel value of the pixel P7 of the band tomographic image DH3 as the pixel value of the pixel P7 of the composite band two-dimensional image CGH0. Since the band tomographic image DH3 in which the tumor and the spicula are detected is selected for the pixel P8, the combination unit 34 sets the pixel value of the pixel P8 of the band tomographic image DH3 as the pixel value of the pixel P8 of the composite band two-dimensional image CGH0.

For the pixel P9, the band tomographic image DH3 in which the tumor has been detected and the band tomographic image DH5 in which the spicula has been detected are selected. In this embodiment, in a case in which different band tomographic images are selected for the tumor, the spicula, and the calcification in the same pixel of the band tomographic images DHj, the pixel values of the band tomographic images determined on the basis of priority given in the order of the tumor, the spicula, and the calcification are assigned. Therefore, the combination unit 34 sets the pixel value of the pixel P9 of the band tomographic image DH5 in which the spicula has been detected as the pixel value of the pixel P9 of the composite band two-dimensional image CGH0.

For the pixel P10, the band tomographic image DH3 in which the tumor has been detected and the band tomographic image DH4 in which the spicula has been detected are selected. Therefore, the combination unit 34 sets the pixel value of the pixel P10 of the band tomographic image DH4 in which the spicula has been detected as the pixel value of the pixel P10 of the composite band two-dimensional image CGH0.

Since the band tomographic image DH4 in which the spicula has been detected is selected for the pixel P11, the combination unit 34 sets the pixel value of the pixel P11 of the band tomographic image DH4 as the pixel value of the pixel P11 of the composite band two-dimensional image CGH0. Since the band tomographic image DH1 in which the calcification has been detected is selected for the pixel P12, the combination unit 34 sets the pixel value of the pixel P12 of the band tomographic image DH1 as the pixel value of the pixel P12 of the composite band two-dimensional image CGH0. Since the band tomographic image DH6 in which the calcification has been detected is selected for the pixel P14, the combination unit 34 sets the pixel value of the pixel P14 of the band tomographic image DH6 as the pixel value of the pixel P14 of the composite band two-dimensional image CGH0.

Then, the combination unit 34 performs frequency synthesis on the composite band two-dimensional image CGML0 in the medium-low frequency band MLf and the composite band two-dimensional image CGH0 in the high frequency band Hf to generate a composite band two-dimensional image CG A method corresponding to the frequency decomposition performed by the frequency decomposition unit 32 may be used as a frequency synthesis method. For example, in a case in which the frequency decomposition is performed by wavelet transform, the frequency synthesis may be performed by inverse wavelet transform.

Figure 18:
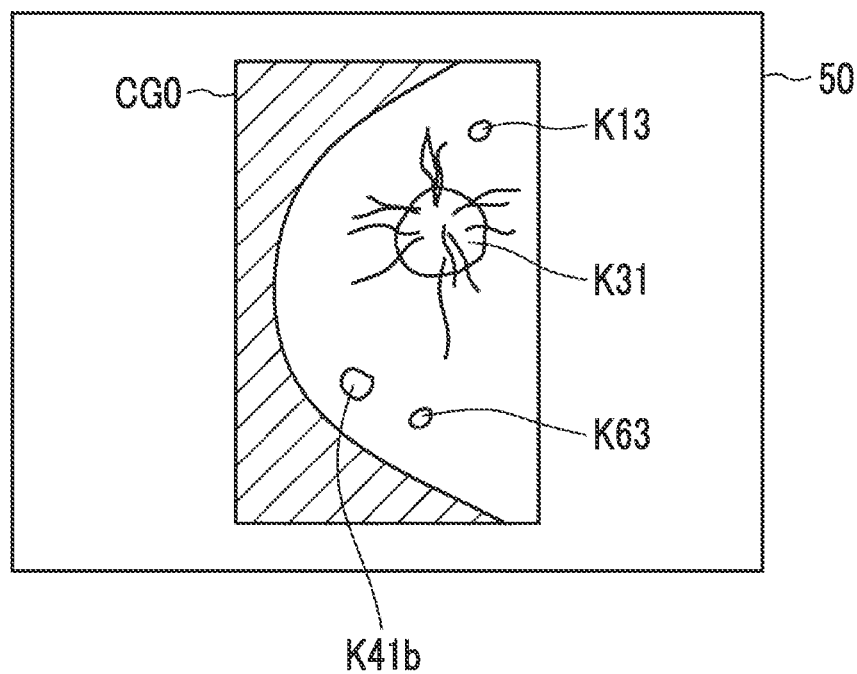
FIG. 18 is a diagram illustrating a composite two-dimensional image display screen.

The display control unit 35 displays the composite two-dimensional image CG0 generated by the combination unit 34 on the display 24. FIG. 18 is a diagram illustrating a composite two-dimensional image display screen. As illustrated in FIG. 18, the composite two-dimensional image CG0 is displayed on a display screen 50 of the display 24. In addition, the composite two-dimensional image CG0 illustrated in FIG. 18 is generated from the tomographic images D1 to D6 illustrated in FIG. 7. The composite two-dimensional image CG0 illustrated in FIG. 18 clearly includes the calcification K13 included in the tomographic image D1, the tumor K31 included in the tomographic image D3, the tumor K41b included in the tomographic image D4, the calcification K63 included in the tomographic image D6, and the spiculae K32, K42, and K52 included in the tomographic images D3 to D5. Further, the illustration of the spiculae K32, K42, and K52 is omitted. The spiculae K32, K42, and K52 partially overlap the tumor K31, and the pixel values of the tumor K31 are replaced with the pixel values of the spiculae K42 and K52 included in the tomographic images D4 and D5.

Figure 19:
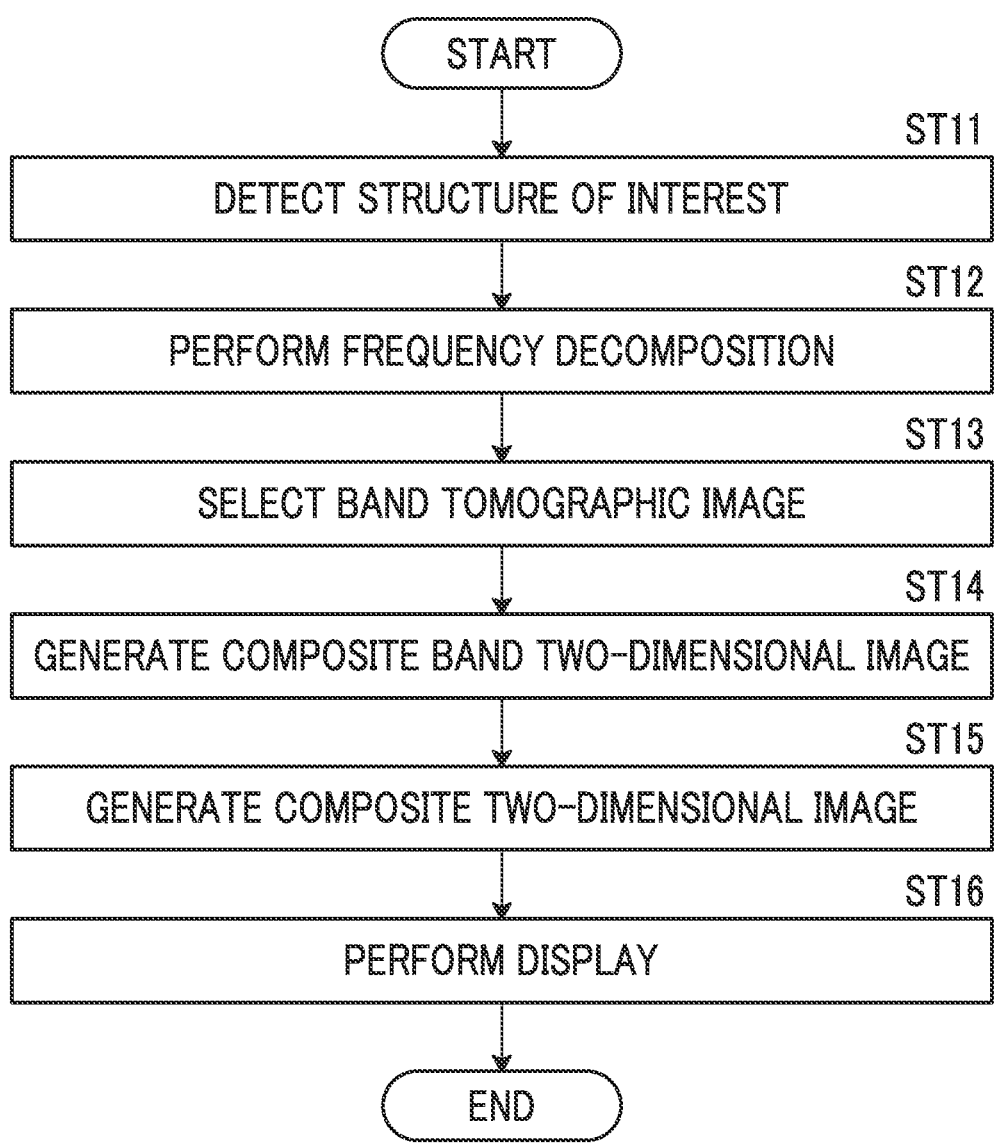
FIG. 19 is a flowchart illustrating a process performed in the first embodiment.

Next, a process performed in the first embodiment will be described. FIG. 19 is a flowchart illustrating the process performed in the first embodiment. In addition, it is assumed that the plurality of tomographic images Dj are acquired in advance and stored in the storage 23. The process is started in a case in which the input device 25 receives a process start instruction from the operator, and the structure-of-interest detection unit 31 detects the structure of interest from each of the plurality of tomographic images Dj (Step ST11). Then, the frequency decomposition unit 32 performs frequency decomposition on each of the plurality of tomographic images Dj to derive a plurality of band tomographic images indicating frequency components in each of a plurality of frequency bands for each of the plurality of tomographic images Dj (Step ST12).

Then, the selection unit 33 selects a band tomographic image corresponding to the tomographic image, in which the structure of interest has been detected, for each corresponding pixel in the plurality of band tomographic images from the plurality of band tomographic images according to the type of the structure of interest and the frequency band (Step ST13).

Then, the combination unit 34 generates the composite band two-dimensional images CGML0 and CGH0 using the selected band tomographic images (Step ST14) and performs frequency synthesis on the composite band two-dimensional images CGML0 and CGH0 to generate the composite two-dimensional image CG0 (Step ST15). Then, the display control unit 35 displays the composite two-dimensional image CG0 on the display 24 (Step ST16). Then, the process ends.

As described above, in the first embodiment, frequency band decomposition is performed on the tomographic image, and a band tomographic image including the structure of interest is selected from a plurality of band tomographic images DMLj and DHj according to the type of the structure of interest and the frequency band. Then, in the region in which the structure of interest has been detected, the composite two-dimensional image CG0 is generated using the selected band tomographic image. Therefore, the composite two-dimensional image CG0 is generated using a smaller number of tomographic images in the region of the structure of interest, as compared to a case in which the composite two-dimensional image is generated by weighting and averaging all of the tomographic images as in the method disclosed in U.S. Pat. No. 9,792,703B. As a result, in the composite two-dimensional image CG0, a fine structure of interest is not blurred. In particular, in the first embodiment, one band tomographic image that best represents the structure of interest is selected for each corresponding pixel in the plurality of band tomographic images. Therefore, it is possible to reduce the blurring of a fine structure of interest in the composite two-dimensional image CG0.

Further, in the first embodiment, in the medium-low frequency band MLf, all of the band tomographic images including the structure of interest are selected for each pixel, which corresponds to the pixels of the composite two-dimensional image CG0, in the plurality of band tomographic images. Therefore, even in a case in which one structure of interest spreads in a direction in which the band tomographic images are arranged, that is, in the depth direction of the breast M, the composite two-dimensional image CG0 is generated using a plurality of selected band tomographic images, which makes it possible to reflect the state of the structure of interest in the depth direction in the composite two-dimensional image CG0.

Furthermore, in the first embodiment, in the high frequency band Hf, one band tomographic image that best represents the structure of interest is selected for each pixel, which corresponds to the pixels of the composite two-dimensional image CG0, in the plurality of band tomographic images. Therefore, even in a case in which one structure of interest spreads in the direction in which the band tomographic images are arranged, that is, in the depth direction of the breast M while two-dimensionally spreading in a direction orthogonal to the optical axis X0 of radiation, a plurality of band tomographic images are selected for the structure of interest. Therefore, the composite two-dimensional image CG0 is generated using a plurality of selected band tomographic images, which makes it possible to reflect the state of the structure of interest, which spreads in the depth direction while spreading two-dimensionally, in the composite two-dimensional image CG0.

Further, in a case in which different band tomographic images are selected for the tumor, the spicula, and the calcification in the same pixel of the band tomographic images DMLj and DHj, the pixel values of the band tomographic images determined on the basis of priority given in the order of the tumor, the spicula, and the calcification are assigned. Here, for the breast M, the tumor has the highest degree of malignancy, followed by the spicula and the calcification in this order. Therefore, the selection of the band tomographic image based on the above-mentioned priority makes it possible to generate the composite two-dimensional image CG0 such that the structure of interest having a higher degree of malignancy is more conspicuous.

Next, a second embodiment of the present disclosure will be described. In addition, the configuration of an image processing device according to the second embodiment is the same as the configuration of the image processing device according to the first embodiment except only the process to be performed. Therefore, the detailed description of the device will not be repeated here. In the second embodiment, the combination unit 34 combines a plurality of tomographic images Dj to generate a first composite two-dimensional image CG1. Then, for each of the structures of interest, the combination unit 34 generates a composite band two-dimensional image for each frequency band using the selected band tomographic image in the pixel of the band tomographic image corresponding to the structure of interest and performs frequency synthesis on the composite band two-dimensional images to generate second composite two-dimensional images CG21, CG22, and CG23 for each of the structures of interest. Further, the combination unit 34 combines the second composite two-dimensional images CG21, CG22, and CG23 for each of the structures of interest with the first composite two-dimensional image CG1 to generate a composite two-dimensional image CG0.

In the second embodiment, first, the combination unit 34 combines the plurality of tomographic images Dj to generate the first composite two-dimensional image CG1. Specifically, the first composite two-dimensional image CG1 is generated by, for example, adding and averaging the pixel values of the corresponding pixels in the plurality of tomographic images Dj.

Further, in the second embodiment, the combination unit 34 generates the second composite two-dimensional images CG21, CG22, and CG23 according to the type of the structure of interest and the frequency band. That is, the second composite two-dimensional image CG21 for the tumor, the second composite two-dimensional image CG22 for the spicula, and the second composite two-dimensional image CG23 for the calcification are generated. First, the generation of the second composite two-dimensional image CG21 for the tumor will be described. In addition, the selection unit 33 selects the band tomographic image for each frequency band for each of the tumor, the spicula, and the calcification as in the first embodiment.

Figure 20:
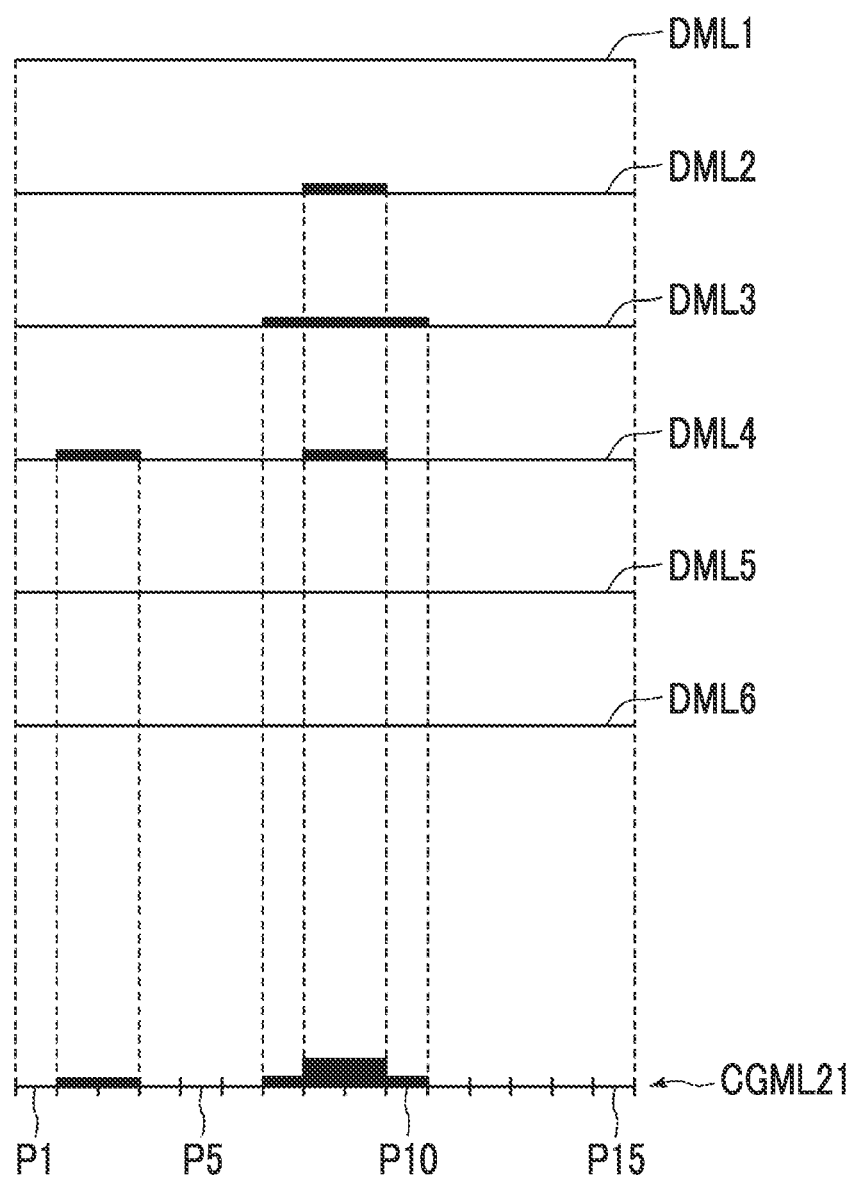
FIG. 20 is a diagram illustrating the generation of a second composite band two-dimensional image in the medium-low frequency band for the tumor.

In the second embodiment, the combination unit 34 generates a second composite band two-dimensional image CGML21 using only the selected band tomographic image only in the pixel in which the tumor has been detected. First, the generation of the second composite band two-dimensional image CGML21 in the medium-low frequency band MLf will be described. In addition, for the tumor, band tomographic images DML2 to DML4 are selected in the medium-low frequency band MLf. FIG. 20 is a diagram illustrating the generation of the second composite band two-dimensional image in the medium-low frequency band for the tumor.

First, for the pixels P1, P4 to P6, and P11 to P15 in which no tumor is detected in any of the band tomographic images DMLj, the combination unit 34 derives the added average value of the pixel values of the band tomographic images DML1 to DML6 and sets the added average value as the pixel values of the pixels P1, P4 to P6, and P11 to P15 of the second composite band two-dimensional image CGML21 in the medium-low frequency band MLf. Since the band tomographic image DML4 is selected for the pixels P2 and P3, the combination unit 34 sets the pixel values of the pixels P2 and P3 of the band tomographic image DML4 as the pixel values of the pixels P2 and P3 of the second composite band two-dimensional image CGML21. Since the band tomographic image DML3 is selected for the pixels P7 and P10 of the band tomographic images DMLj, the combination unit 34 sets the pixel values of the pixels P7 and P10 of the band tomographic image DML3 as the pixel values of the pixels P7 and P10 of the second composite band two-dimensional image CGML21. Since the band tomographic images DML2 to DML4 are selected for the pixels P8 and P9 of the band tomographic images DMLj, the combination unit 34 sets the added value of the pixel values of the pixels P8 and P9 of the band tomographic images DML2 to DML4 as the pixel values of the pixels P8 and P9 of the second composite band two-dimensional image CGML21. In addition, a weighted added value, a weighted average value, or the like may be used instead of the added value. In this case, a weight for the band tomographic image DML3 may be larger than those for the band tomographic images DML2 and DML4.

Figure 21:
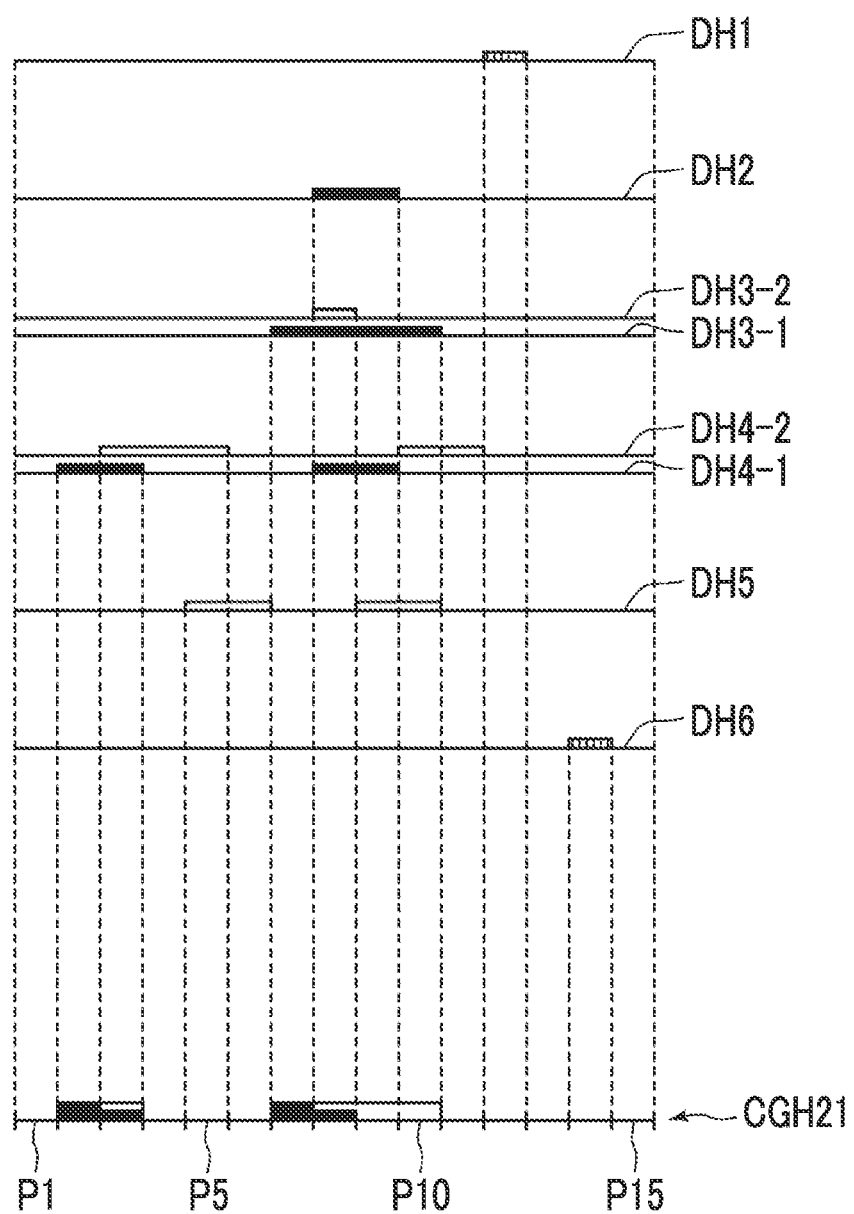
FIG. 21 is a diagram illustrating the generation of the second composite band two-dimensional image in the high frequency band for the tumor.

Next, the generation of a second composite band two-dimensional image CGH21 in the high frequency band Hf for the tumor will be described. FIG. 21 is a diagram illustrating the generation of the second composite band two-dimensional image in the high frequency band for the tumor. As illustrated in FIG. 21, for the pixels P1, P4 to P6, and P11 to P15 in which no tumor is detected in any of the band tomographic images DHj, the combination unit 34 derives the added average value of the pixel values of the band tomographic images DH1 to DH6 and sets the added average value as the pixel values of the pixels P1, P4 to P6, and P11 to P15 of the second composite band two-dimensional image CGH21 in the high frequency band Hf. Since the band tomographic image DH4 is selected for the pixels P2 and P3, the combination unit 34 sets the pixel values of the pixels P2 and P3 of the band tomographic image DH4 as the pixel values of the pixels P2 and P3 of the second composite band two-dimensional image CGH21. Since the band tomographic image DH3 is selected for the pixels P7 to P10 of the band tomographic images DHj, the combination unit 34 sets the pixel values of the pixels P7 to P10 of the band tomographic image DH3 as the pixel values of the pixels P7 to P10 of the second composite band two-dimensional image CGH21.

Then, the combination unit 34 performs frequency synthesis on the second composite band two-dimensional image CGML21 in the medium-low frequency band MLf and the second composite band two-dimensional image CGH2 in the high frequency band Hf for the tumor to generate the second composite two-dimensional image CG21 for the tumor.

Next, the generation of the second composite two-dimensional image CG22 for the spicula will be described. In the second embodiment, also for the spicula, the combination unit 34 generates the second composite band two-dimensional image CG22 using only the selected band tomographic image only in the pixel in which the spicula has been detected. In addition, the structure of the spicula is included only in the band tomographic images DHj in the high frequency band Hf. Therefore, for the band tomographic images DMLj in the medium-low frequency band MLf, the combination unit 34 sets the added average value of the pixel values of all of the pixels P1 to P15 as the pixel values of the pixels P1 to P15 of a second composite band two-dimensional image CGML22 in the medium-low frequency band MLf.

Figure 22:
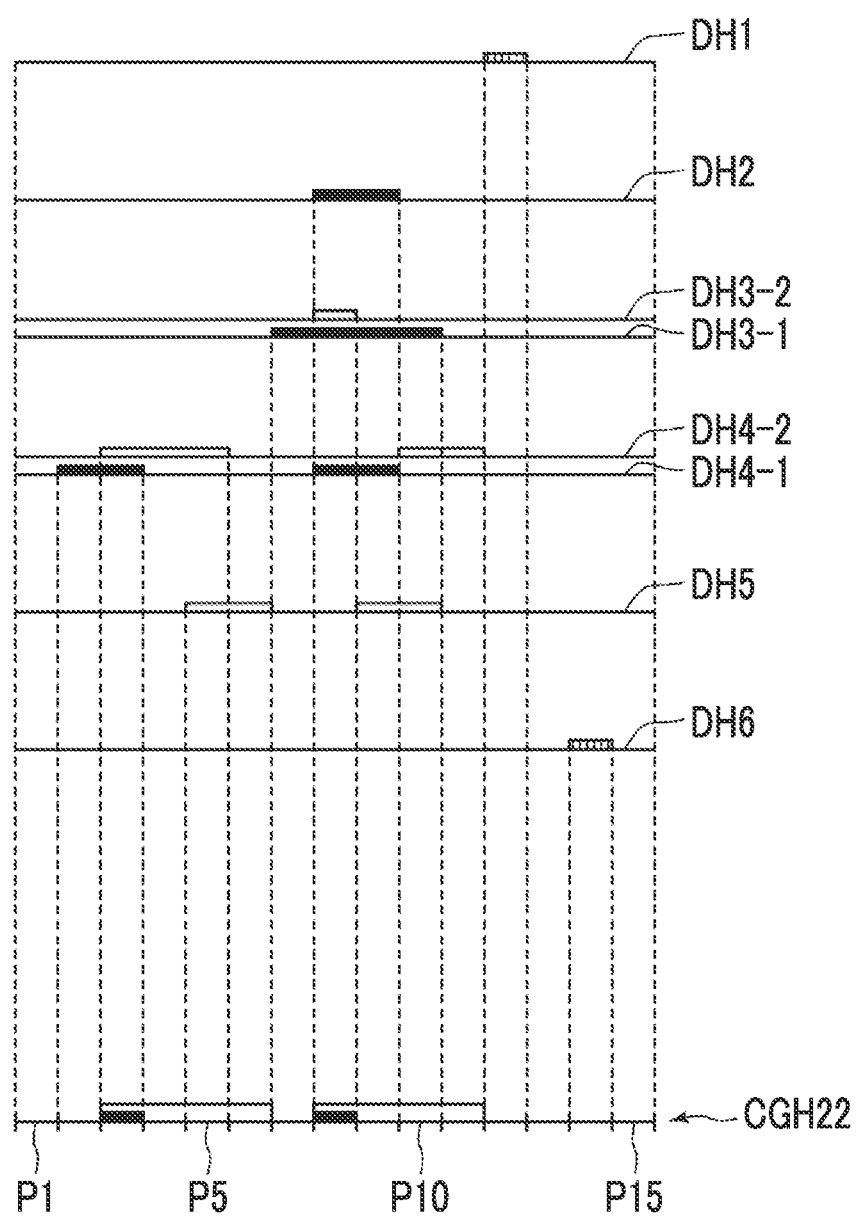
FIG. 22 is a diagram illustrating the generation of the second composite band two-dimensional image in the high frequency band for the spicula.

FIG. 22 is a diagram illustrating the generation of the second composite band two-dimensional image in the high frequency band for the spicula. As illustrated in FIG. 22, for the pixels P1, P2, P7, and P12 to P15 in which the spicula is not detected in any of the band tomographic images DHj, the combination unit 34 derives the added average value of the pixel values of the band tomographic images DH1 to DH6 and sets the added average value as the pixel values of the pixels P1, P2, P7, and P12 to P15 of a second composite band two-dimensional image CGH22 in the high frequency band Hf. Since the band tomographic image DH4 is selected for the pixels P3 to P5, P10, and P11, the combination unit 34 sets the pixel values of the pixels P3 to P5, P10, and P11 of the band tomographic image DH4 as the pixel values of the pixels P3 to P5, P10, and P11 of the second composite band two-dimensional image CGH22. Since the band tomographic image DH5 is selected for the pixels P6 and P9, the combination unit 34 sets the pixel values of the pixels P6 and P9 of the band tomographic image DH5 as the pixel values of the pixels P6 and P9 of the second composite band two-dimensional image CGH22. Since the band tomographic image DH3 is selected for the pixel P8, the combination unit 34 uses the pixel value of the pixel P8 of the band tomographic image DH3 as the pixel value of the pixel P8 of the second composite band two-dimensional image CGH22.

Then, the combination unit 34 performs frequency synthesis on the second composite band two-dimensional image CGML22 in the medium-low frequency band MLf and the second composite band two-dimensional image CGH22 in the high frequency band Hf for the spicula to generate the second composite two-dimensional image CG22 for the spicula.

Next, the generation of the second composite two-dimensional image CG23 for the calcification will be described. In the second embodiment, also for the calcification, the combination unit 34 generates the second composite band two-dimensional image CG23 using only the selected band tomographic image only in the pixel in which the calcification has been detected. In addition, the structure of the calcification is included only in the band tomographic images DHj in the high frequency band Hf Therefore, for the band tomographic images DMLj in the medium-low frequency band MLf, the combination unit 34 sets the added average value of the pixel values of all of the pixels P1 to P15 as the pixel values of the pixels P1 to P15 of a second composite band two-dimensional image CGML23 in the medium-low frequency band MLf.

Figure 23:
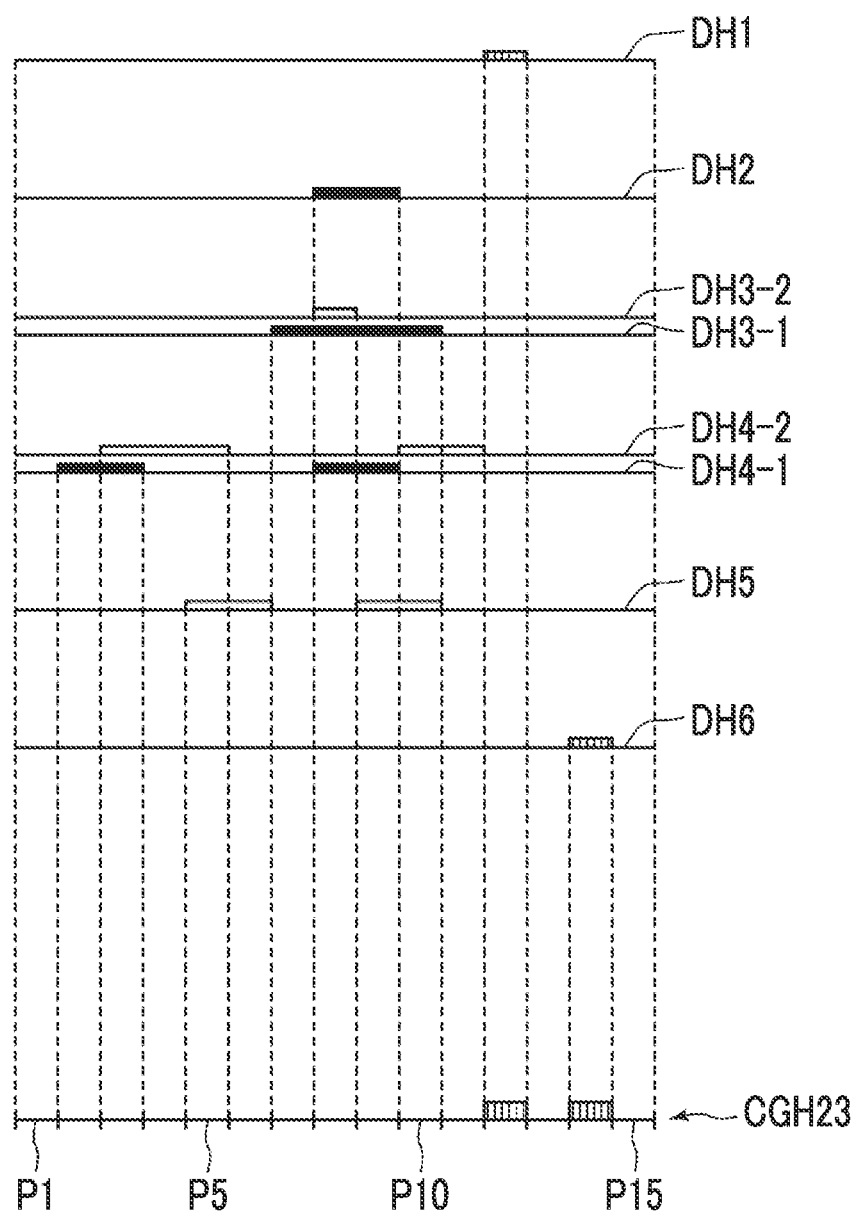
FIG. 23 is a diagram illustrating the generation of the second composite band two-dimensional image in the high frequency band for the calcification.

FIG. 23 is a diagram illustrating the generation of the second composite band two-dimensional image in the high frequency band for the calcification. As illustrated in FIG. 23, for the pixels P1 to P11, P13, and P15 in which the calcification is not detected in any of the band tomographic images DHj, the combination unit 34 derives the added average value of the pixel values of the band tomographic images DH1 to DH6 and sets the added average value as the pixel values of the pixels P1 to P11, P13, and P15 of a second composite band two-dimensional image CGH23 in the high frequency band Hf Since the band tomographic image DH1 is selected for the pixel P12, the combination unit 34 sets the pixel value of the pixel P12 of the band tomographic image DH1 in the high frequency band Hf as the pixel value of the pixel P12 of the second composite band two-dimensional image CGH23. Since the band tomographic image DH6 is selected for the pixel P14, the combination unit 34 sets the pixel value of the pixel P14 of the band tomographic image DH6 as the pixel value of the pixel P14 of the second composite band two-dimensional image CGH23.

Then, the combination unit 34 performs frequency synthesis on the second composite band two-dimensional image CGML23 in the medium-low frequency band MLf and the second composite band two-dimensional image CGH23 in the high frequency band Hf for the calcification to generates the second composite two-dimensional image CG23 for the calcification.

Figure 24:
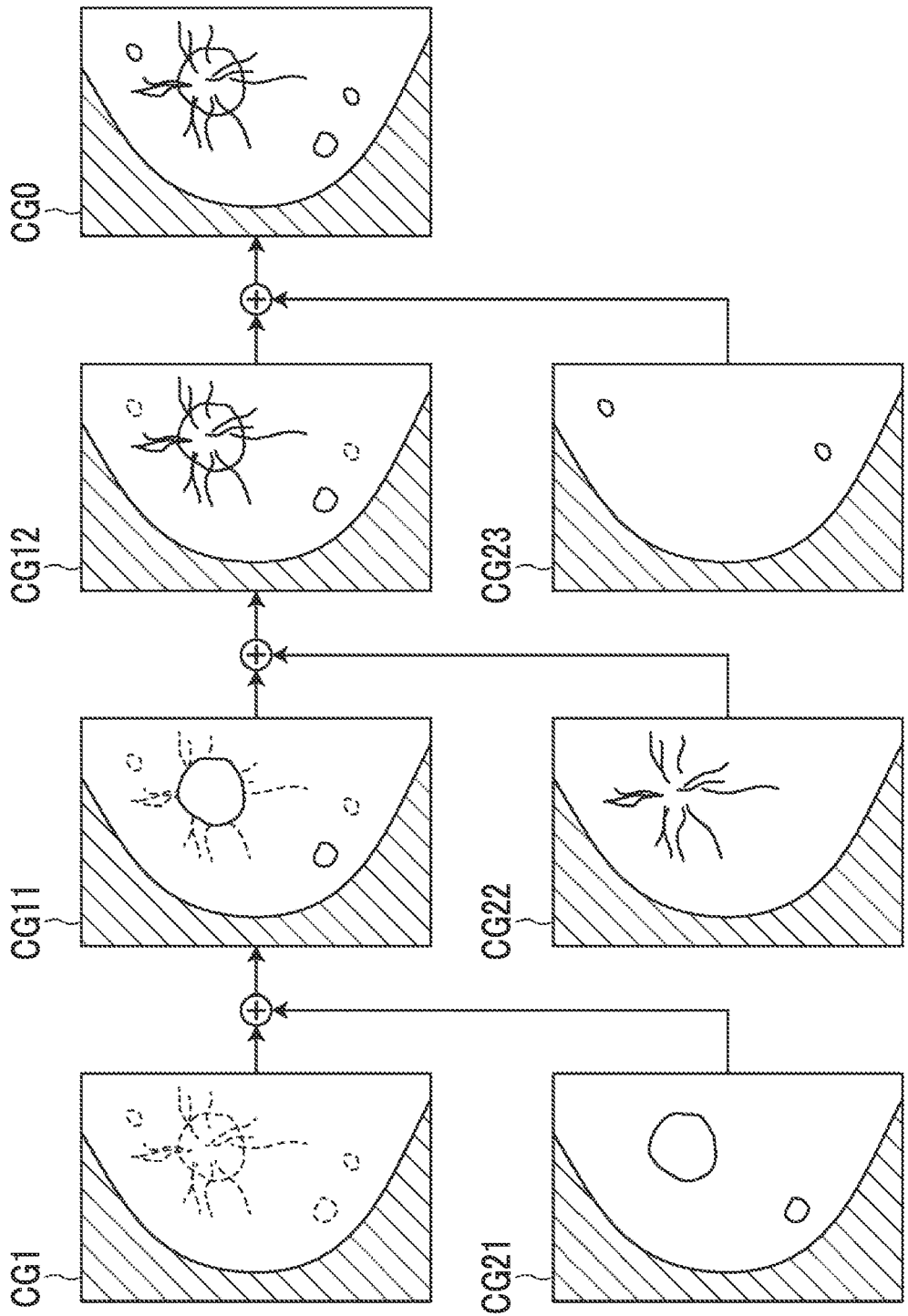
FIG. 24 is a diagram illustrating the generation of a composite two-dimensional image CG0 in a second embodiment.

The combination unit 34 sequentially combines the second composite two-dimensional image CG21 for the tumor, the second composite two-dimensional image CG22 for the spicula, and the second composite two-dimensional image CG23 for the calcification generated as described above with the first composite two-dimensional image CG1 to generate the composite two-dimensional image CG0. FIG. 24 is a diagram illustrating the generation of the composite two-dimensional image CG0 in the second embodiment. As illustrated in FIG. 24, first, the combination unit 34 replaces the region of the tumor in the first composite two-dimensional image CG1 with the region of the tumor in the second composite two-dimensional image CG21 for the tumor to combine the second composite two-dimensional image CG21 for the tumor with the first composite two-dimensional image CG1. As a result, an intermediate composite two-dimensional image CG11 is generated.

Then, the combination unit 34 replaces the region of the spicula in the intermediate composite two-dimensional image CG11 with the region of the spicula in the second composite two-dimensional image CG22 for the spicula to combine the second composite two-dimensional image CG22 for the spicula with the intermediate composite two-dimensional image CG11. As a result, an intermediate composite two-dimensional image CG12 is generated.

Further, the combination unit 34 replaces the region of the calcification in the intermediate composite two-dimensional image CG12 with the region of the calcification in the second composite two-dimensional image CG23 for the calcification to combine the second composite two-dimensional image CG23 for the calcification with the intermediate composite two-dimensional image CG12. As a result, the composite two-dimensional image CG0 according to the second embodiment is generated.

Figure 25:
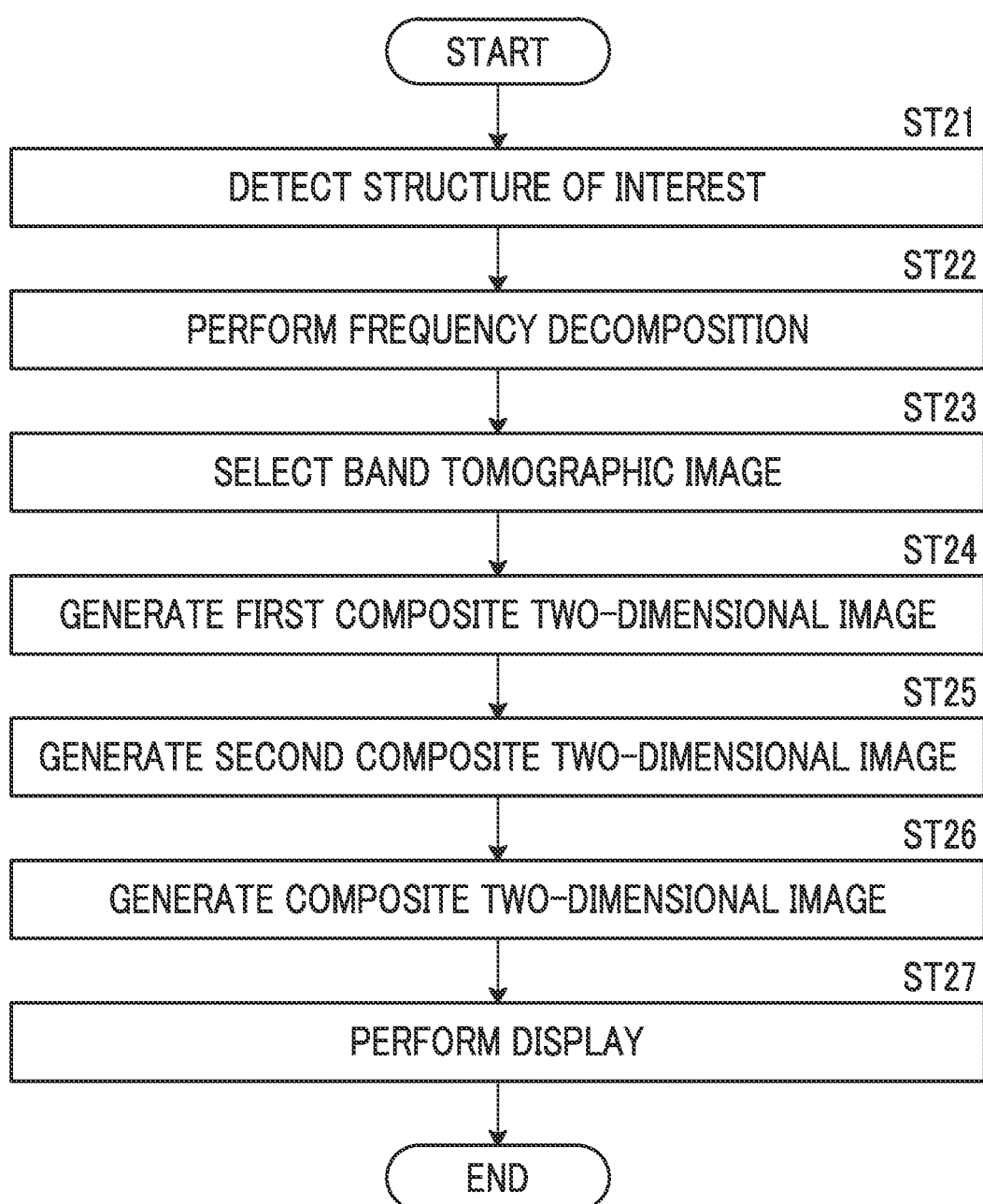
FIG. 25 is a flowchart illustrating a process performed in the second embodiment.

Next, a process performed in the second embodiment will be described. FIG. 25 is a flowchart illustrating the process performed in the second embodiment. In addition, it is assumed that the plurality of tomographic images Dj are acquired in advance and stored in the storage 23. The process is started in a case in which the input device 25 receives a process start instruction from the operator, and the structure-of-interest detection unit 31 detects the structure of interest from the plurality of tomographic images Dj (Step ST21). Then, the frequency decomposition unit 32 performs frequency decomposition on each of the plurality of tomographic images Dj to derive a plurality of band tomographic images indicating frequency components in each of a plurality of frequency bands for each of the plurality of tomographic images Dj (Step ST22).

Then, the selection unit 33 selects a band tomographic image corresponding to the tomographic image, in which the structure of interest has been detected, from the plurality of band tomographic images for each corresponding pixel of the plurality of band tomographic images according to the type of the structure of interest and the frequency band (Step ST23).

Then, the combination unit 34 generates the first composite two-dimensional image CG1 from the plurality of tomographic images Dj (Step ST24). In addition, the process in Step ST24 may be performed before each of the processes in Steps ST21 to ST23 or may be performed in parallel to these processes. Then, the combination unit 34 generates the second composite two-dimensional images CG21, CG22, and CG23 for the tumor, the spicula, and the calcification, respectively (Step ST25). Further, the combination unit 34 sequentially combines the second composite two-dimensional images CG21, CG22, and CG23 for the tumor, the spicula, and the calcification with the first composite two-dimensional image CG1 to generate the composite two-dimensional image CG0 (Step ST26). Then, the display control unit 35 displays the composite two-dimensional image CG0 on the display 24 (Step ST27). Then, the process ends.

Next, a third embodiment of the present disclosure will be described. In addition, the configuration of an image processing device according to the third embodiment is the same as the configuration of the image processing device according to the second embodiment except only the process to be performed. Therefore, the detailed description of the device will not be repeated here. In the third embodiment, the combination unit 34 combines the plurality of tomographic images Dj to generate the first composite two-dimensional image CG1. Then, the combination unit 34 generates a composite band two-dimensional image for each frequency band using the selected band tomographic image in the pixels of the composite two-dimensional image CG0 which correspond to the tumor and the spicula among the tumor, the spicula, and the calcification and performs frequency synthesis on the composite band two-dimensional images to generate the second composite two-dimensional images CG21 and CG22. Meanwhile, the combination unit 34 extracts the region of the calcification as a calcification region from the first composite two-dimensional image CG1. Further, the combination unit 34 combines the second composite two-dimensional images CG21 and G22 for the tumor and the spicula with the first composite two-dimensional image CG1 and further combines the calcification region to generate the composite two-dimensional image CG0.

In addition, in the third embodiment, the generation of the first composite two-dimensional image CG1, the generation of the second composite band two-dimensional image CG21 for the tumor, and the generation of the second composite two-dimensional image CG22 for the spicula are performed by the combination unit 34 in the same manner as in the second embodiment.

Figure 26:
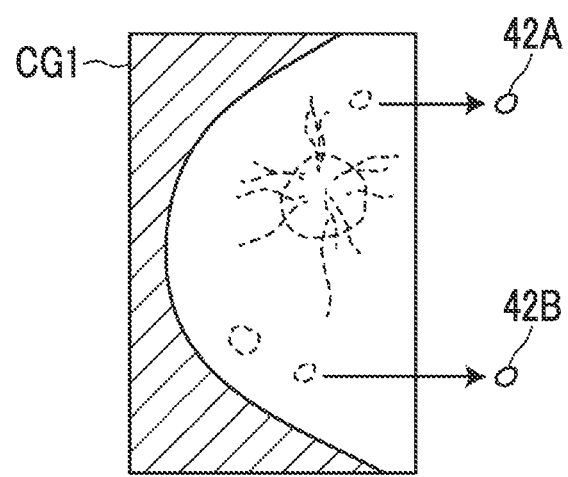
FIG. 26 is a diagram illustrating the extraction of a calcification region.

FIG. 26 is a diagram illustrating the extraction of the calcification region from the first composite two-dimensional image CG1. The combination unit 34 extracts regions corresponding to the calcification regions detected from each of the tomographic images Dj by the structure-of-interest detection unit 31 as calcification regions 42A and 42B from the first composite two-dimensional image CG1.

Figure 27:
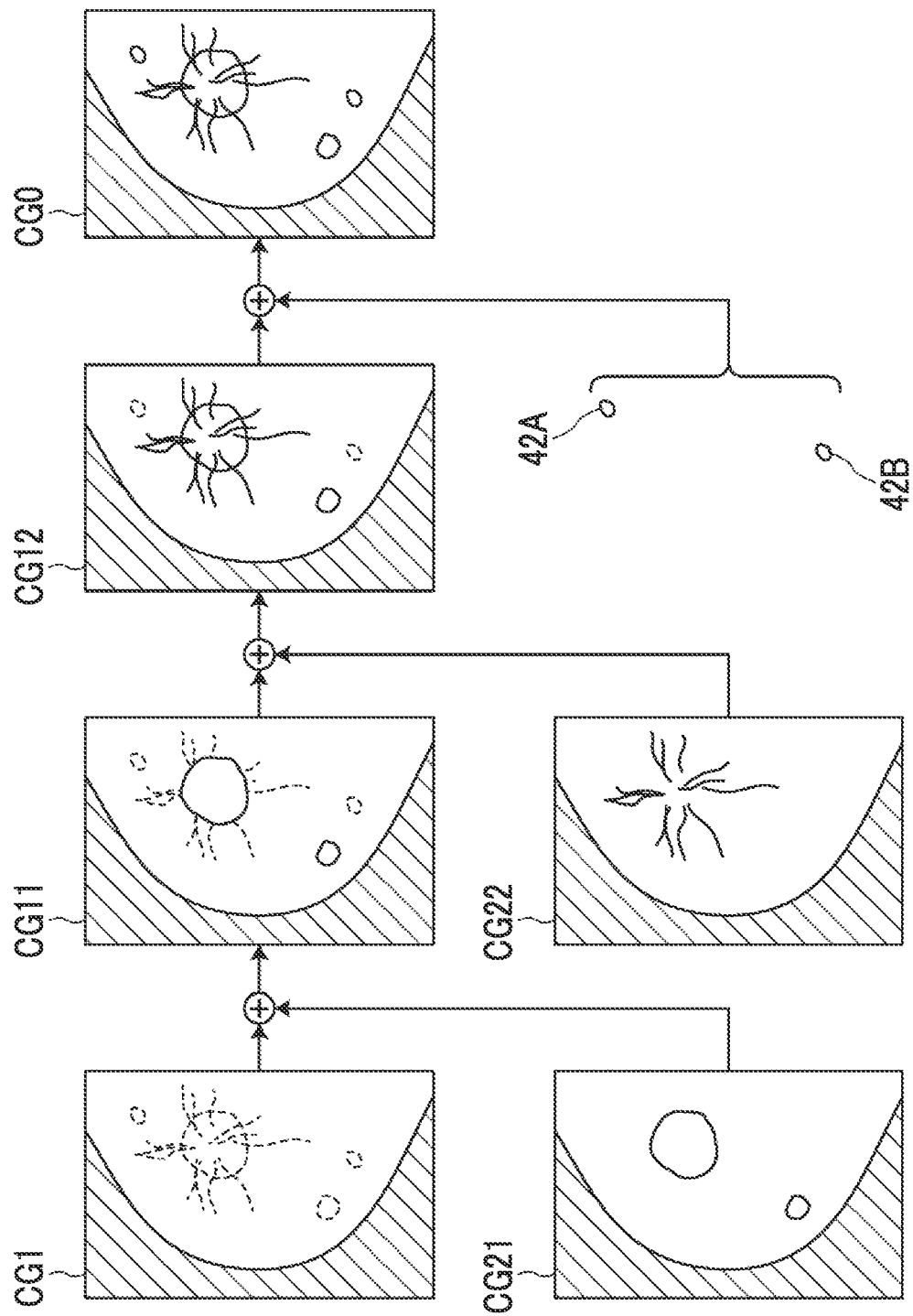
FIG. 27 is a diagram illustrating the generation of the composite two-dimensional image in a third embodiment.

FIG. 27 is a diagram illustrating the generation of the composite two-dimensional image CG0 in the third embodiment. As illustrated in FIG. 27, first, the combination unit 34 replaces the region of the tumor in the first composite two-dimensional image CG1 with the region of the tumor in the second composite two-dimensional image CG21 for the tumor to combine the second composite two-dimensional image CG21 for the tumor with the first composite two-dimensional image CG1. As a result, an intermediate composite two-dimensional image CG11 is generated.

Then, the combination unit 34 replaces the region of the spicula in the intermediate composite two-dimensional image CG11 with the region of the spicula in the second composite two-dimensional image CG22 for the spicula to combine the second composite two-dimensional image CG22 for the spicula with the intermediate composite two-dimensional image CG11. As a result, an intermediate composite two-dimensional image CG12 is generated.

Further, in the third embodiment, the combination unit 34 replaces the calcification region of the intermediate composite two-dimensional image CG12 with the calcification regions 42A and 42B to combine the calcification regions 42A and 42B with the intermediate composite two-dimensional image CG12. As a result, the composite two-dimensional image CG0 according to the third embodiment is generated.

Figure 28:
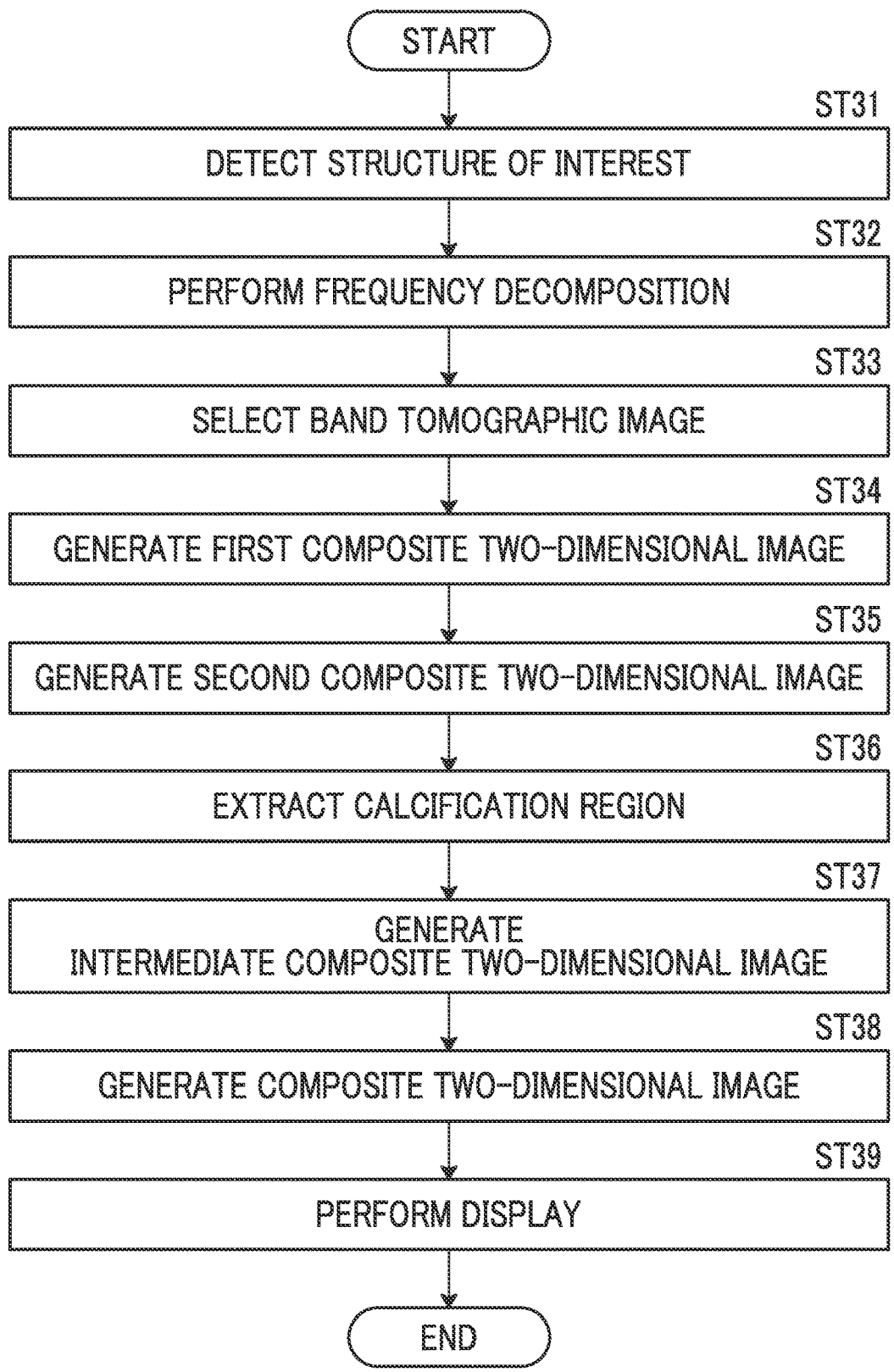
FIG. 28 is a flowchart illustrating a process performed in the third embodiment.

Next, a process performed in the third embodiment will be described. FIG. 28 is a flowchart illustrating the process performed in the third embodiment. In addition, it is assumed that the plurality of tomographic images Dj are acquired in advance and stored in the storage 23. The process is started in a case in which the input device 25 receives a process start instruction from the operator, and the structure-of-interest detection unit 31 detects the structure of interest from each of the plurality of tomographic images Dj (Step ST31). Then, the frequency decomposition unit 32 performs frequency decomposition on each of the plurality of tomographic images Dj to derive a plurality of band tomographic images indicating frequency components in each of a plurality of frequency bands for each of the plurality of tomographic images Dj (Step ST32).

Then, the selection unit 33 selects a band tomographic image corresponding to the tomographic image, in which the structure of interest has been detected, from the plurality of band tomographic images for each corresponding pixel of the plurality of band tomographic images according to the type of the structure of interest and the frequency band (Step ST33).

Then, the combination unit 34 generates the first composite two-dimensional image CG1 from the plurality of tomographic images Dj (Step ST34). In addition, the process in Step ST34 may be performed before each of the processes in Steps ST31 to ST33 or may be performed in parallel to these processes. Then, the combination unit 34 generates the second composite two-dimensional images CG21 and CG22 for the tumor and the spicula, respectively (Step ST35). Further, the combination unit 34 extracts the calcification regions 42A and 42B from the first composite two-dimensional image CG1 (Step ST36). Furthermore, the process in Step ST36 may be performed before any process after the first composite two-dimensional image CG1 is generated or may be performed in parallel to any process.

Then, the combination unit 34 sequentially combines the second composite two-dimensional images CG21 and CG22 for the tumor and the spicula with the first composite two-dimensional image CG1 to generate the intermediate composite two-dimensional image CG12 (Step ST37). Then, the combination unit 34 combines the calcification regions 42A and 42B with the intermediate composite two-dimensional image CG12 to generate the composite two-dimensional image CG0 (Step ST38). Further, the display control unit 35 displays the composite two-dimensional image CG0 on the display 24 (Step ST39). Then, the process ends.

In each of the above-described embodiments, for the tumor, in the medium-low frequency band MLf, all of the band tomographic images including the tumor are selected for each pixel, which corresponds to the pixels of the composite two-dimensional image CG0, in the plurality of band tomographic images. Further, in the high frequency band Hf, one band tomographic image that best represents the tumor is selected for each pixel, which corresponds to the pixels of the composite two-dimensional image CG0, in the plurality of band tomographic images. However, the selection of the band tomographic image is not limited thereto. For the tumor, only in the medium-low frequency band MLf, all of the band tomographic images including the tumor may be selected for each pixel, which corresponds to the pixels of the composite two-dimensional image CG0, in the plurality of band tomographic images. Hereinafter, this will be described as a fourth embodiment.

Figure 29:
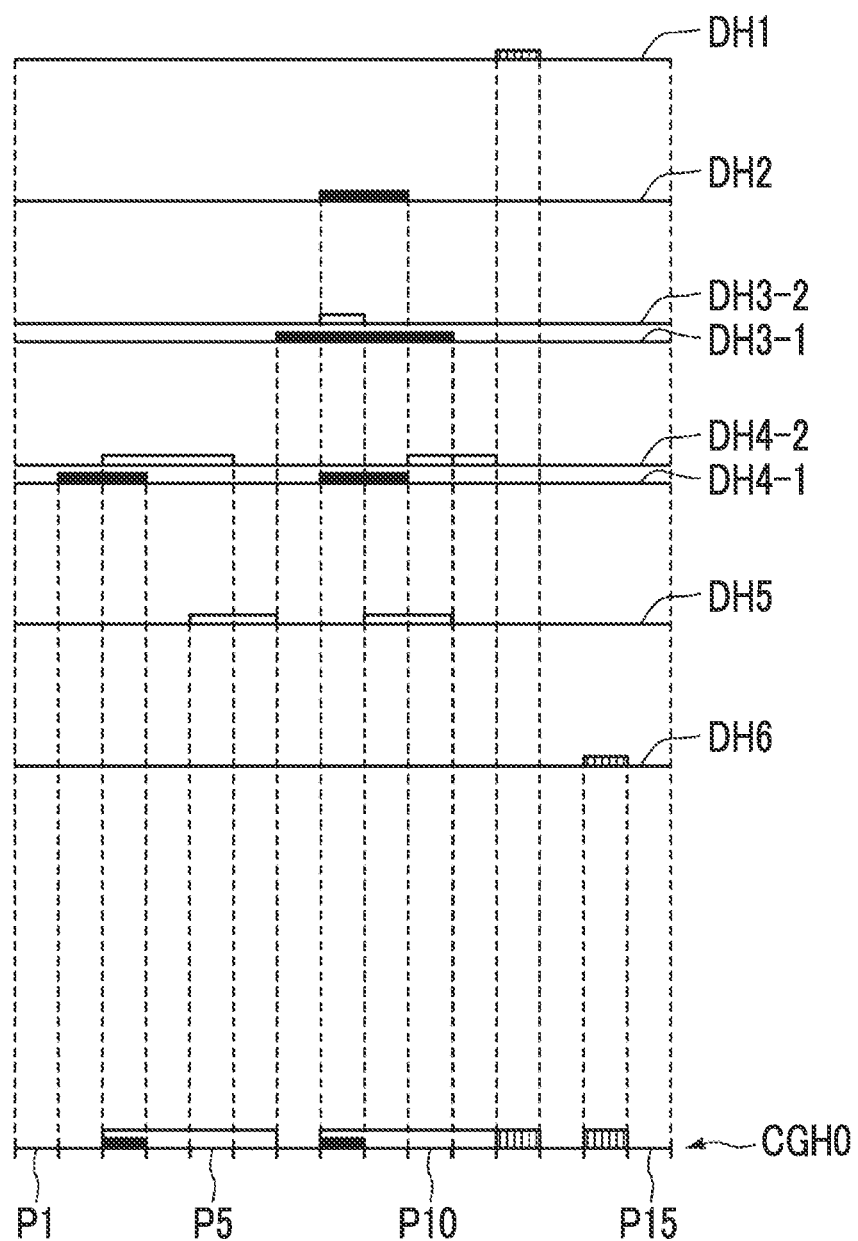
FIG. 29 is a diagram illustrating the generation of the composite band two-dimensional image in the high frequency band in a fourth embodiment.

In a case in which the band tomographic image is selected as in the fourth embodiment and the process according to the first embodiment is performed, the combination unit 34 generates the composite band two-dimensional image CGML0 in the medium-low frequency band MLf as in the first embodiment. On the other hand, in the fourth embodiment, the band tomographic image for the tumor is not selected in the high frequency band Hf Therefore, the band tomographic images DH2 and DH3-1 are not selected even for the pixels P2 and P7 illustrated in FIG. 17. Therefore, in a case in which the process according to the first embodiment is performed in the fourth embodiment, the combination unit 34 derives the added average value of the pixel values of the pixels P2 and P7 in all of the band tomographic images DH1 to DH6 and sets the added average value as the pixel values of the pixels P2 and P7 of the composite band two-dimensional image CGH0 in the high frequency band Hf as illustrated in FIG. 29, similarly to the pixels P1, P13, and P15.

Figure 30:
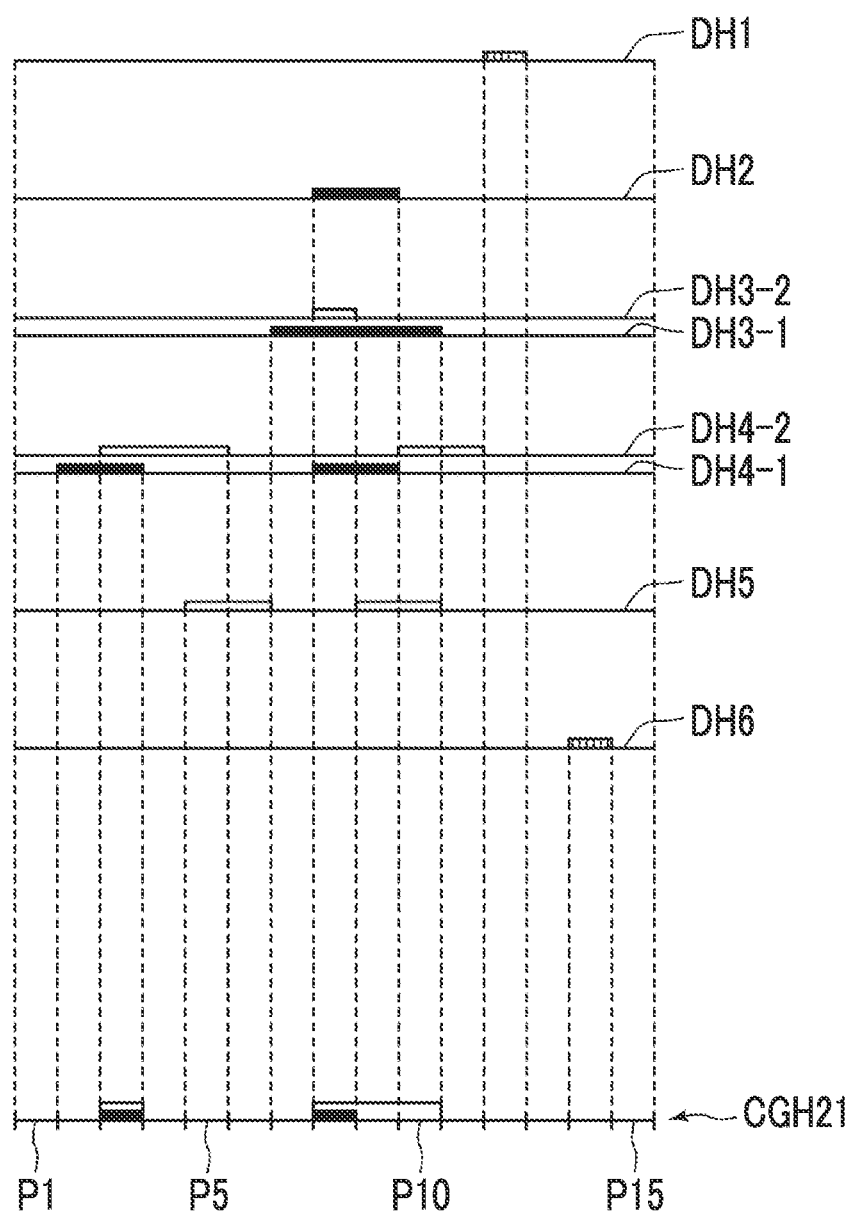
FIG. 30 is a diagram illustrating the generation of the second composite band two-dimensional image in the high frequency band for the tumor in the fourth embodiment.

Meanwhile, in a case in which the band tomographic image is selected in the fourth embodiment and the process according to the second embodiment is performed, the combination unit 34 generates the composite band two-dimensional image CGML21 in the medium-low frequency band MLf for the tumor as in the second embodiment. On the other hand, in the fourth embodiment, the band tomographic image for the tumor is not selected in the high frequency band Hf Therefore, the band tomographic images DH2 and DH3-1 are not selected even for the pixels P2 and P7 illustrated in FIG. 21. Therefore, in a case in which the process according to the second embodiment is performed in the fourth embodiment, the combination unit 34 derives the added average value of the pixel values of the pixels P2 and P7 in all of the band tomographic images DH1 to DH6 and sets the added average value as the pixel values of the pixels P2 and P7 of the second composite band two-dimensional image CGH21 in the high frequency band Hf for the tumor as illustrated in FIG. 30, similarly to the pixels P1, P4 to P6, and P11 to P15.

Further, for the tumor, in both the high frequency band Hf and the medium-low frequency band MLf, one band tomographic image that best represents the tumor may be selected for each pixel, which corresponds to the pixels of the composite two-dimensional image CG0, in the plurality of band tomographic images. Hereinafter, this will be described as a fifth embodiment.

In the fifth embodiment, the selection unit 33 selects one band tomographic image that best represents the tumor for each pixel which corresponds to the pixels of the composite two-dimensional image CG0 in the medium-low frequency band MLf for the tumor. Specifically, the selection unit 33 selects the band tomographic image DML4 for the pixel P2 and P3 illustrated in FIG. 10 and selects the band tomographic image DML3 for the pixels P7 to P10. Further, in the fifth embodiment, the band tomographic images DML2 and DML4 illustrated in FIG. 10 are not selected for the pixels P8 and P9. In the high frequency band Hf, the band tomographic image is selected in the same manner as in each of the above-described embodiments.

Figure 31:
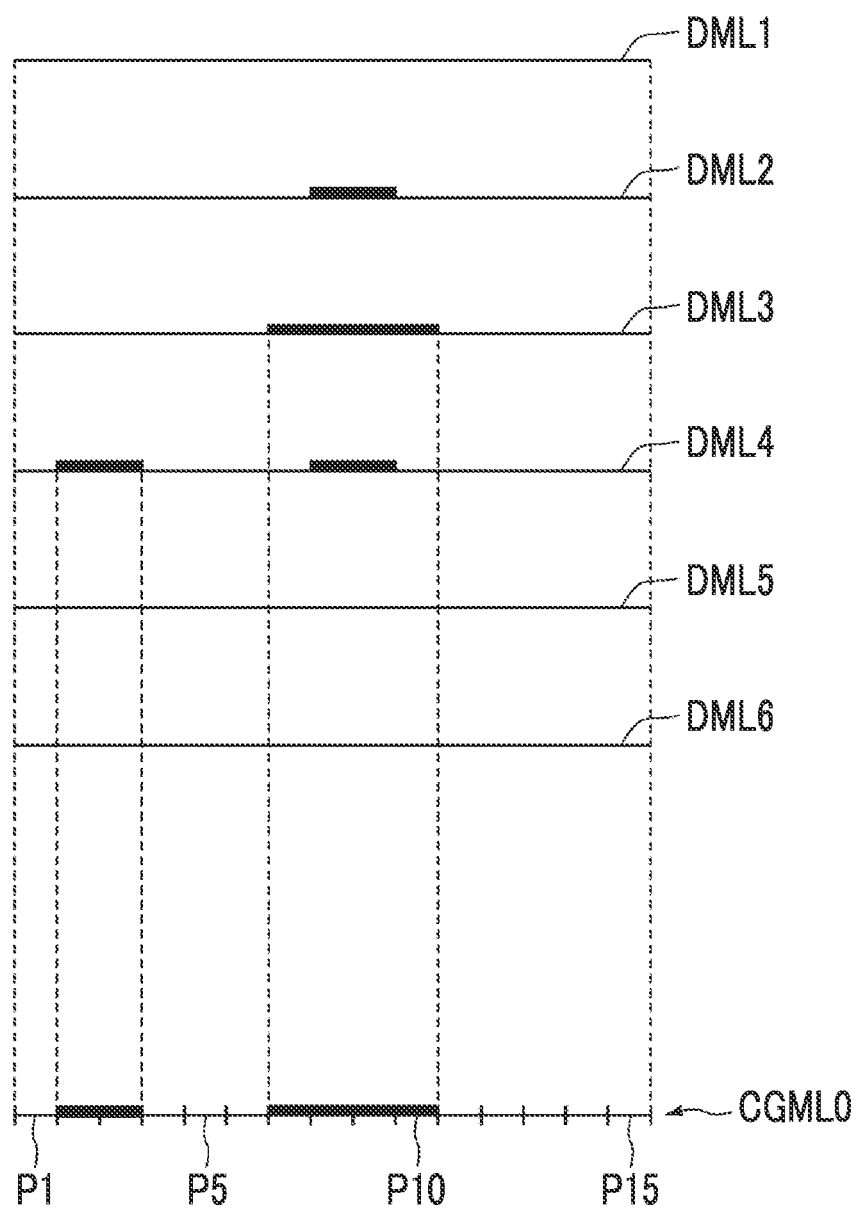
FIG. 31 is a diagram illustrating the generation of the composite band two-dimensional image in the high frequency band in a fifth embodiment.

In a case in which the band tomographic image is selected as in the fifth embodiment and the process according to the first embodiment is performed, the combination unit 34 generates the composite band two-dimensional image CGH0 in the high frequency band Hf as in the first embodiment. Meanwhile, in the fifth embodiment, for the tumor, even in the medium-low frequency band MLf, one band tomographic image that best represents the tumor is selected for each pixel, which corresponds to the pixels of the composite two-dimensional image CG0, in the plurality of band tomographic images. Therefore, only one band tomographic image DML3 is selected even for the pixels P8 and P9 illustrated in FIG. 16. Therefore, in a case in which the process according to the first embodiment is performed in the fifth embodiment, for the pixels P8 and P9, the combination unit 34 sets the pixel values of the pixels P8 and P9 of the band tomographic image DML3 as the pixel values of the pixels P8 and P9 of the composite band two-dimensional image CGML0 in the medium-low frequency band MLf as illustrated in FIG. 31.

Figure 32:
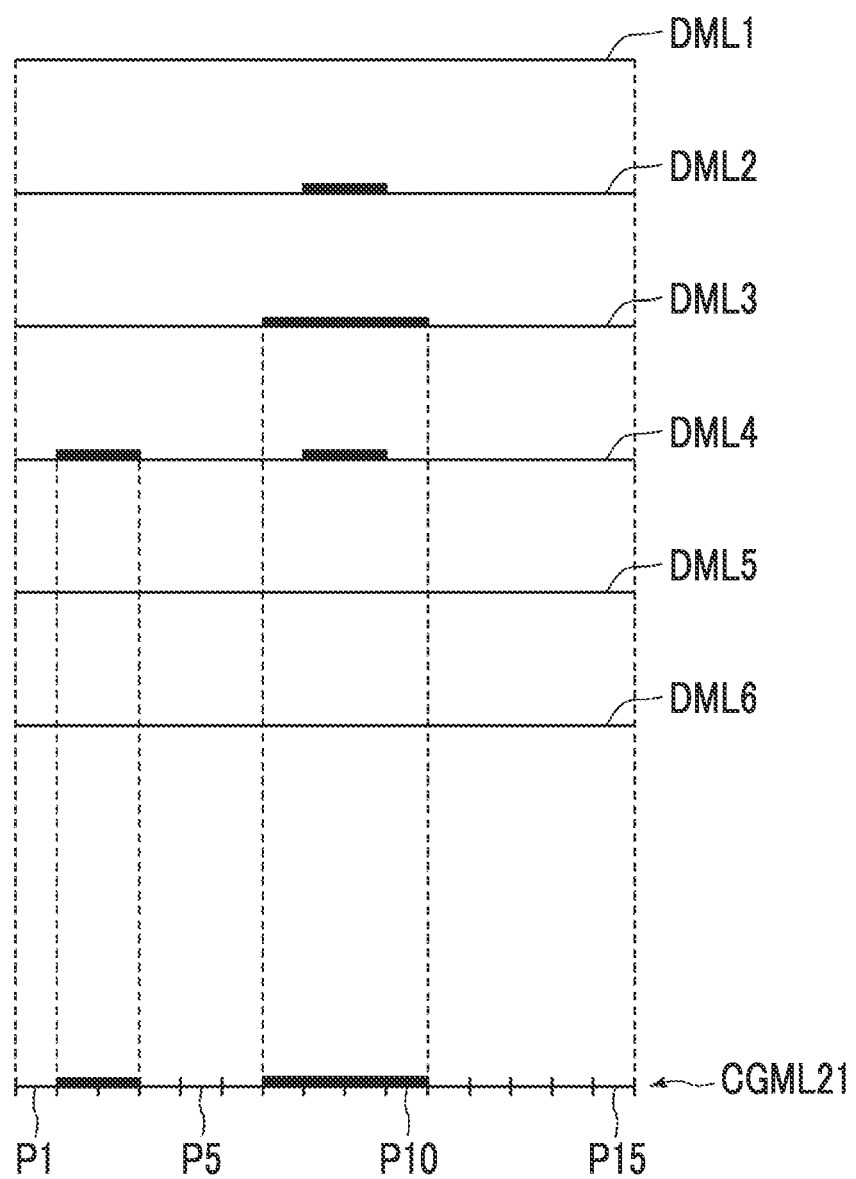
FIG. 32 is a diagram illustrating the generation of the second composite band two-dimensional image in the high frequency band for the tumor in the fifth embodiment.

Meanwhile, in a case in which the band tomographic image is selected as in the fifth embodiment and the process according to the second embodiment is performed, the combination unit 34 generates the second composite band two-dimensional image CGH21 in the high frequency band Hf for the tumor as in the second embodiment. Meanwhile, in the fifth embodiment, even in the medium-low frequency band MLf, one band tomographic image that best represents the tumor is selected for each pixel, which corresponds to the pixels of the composite two-dimensional image CG0, in the plurality of band tomographic images. Therefore, only one band tomographic image DML3 is selected even for the pixels P8 and P9 illustrated in FIG. 20. Therefore, in a case in which the process according to the second embodiment is performed in the fifth embodiment, for the pixels P8 and P9, the combination unit 34 sets the pixel values of the pixels P8 and P9 of the band tomographic image DML3 as the pixel values of the pixels P8 and P9 of the composite band two-dimensional image CGML21 in the medium-low frequency band MLf for the tumor as illustrated in FIG. 32.

Further, only in the medium-low frequency band MLf, one band tomographic image that best represents the tumor may be selected for each pixel, which corresponds to the pixels of the composite two-dimensional image CG0, in the plurality of band tomographic images. Hereinafter, this will be described as a sixth embodiment.

In the sixth embodiment, the selection unit 33 selects one band tomographic image that best represents the tumor for each pixel, which corresponds to the pixels of the composite two-dimensional image CG0, only in the medium-low frequency band MLf for the tumor. Specifically, the selection unit 33 selects the band tomographic image DML4 for the pixel P2 and P3 illustrated in FIG. 10 and selects the band tomographic image DML3 for the pixels P7 to P10. Meanwhile, in the sixth embodiment, the band tomographic image is not selected in the high frequency band Hf for the tumor.

In a case in which the band tomographic image is selected as in the sixth embodiment and the process according to the first embodiment is performed, the combination unit 34 generates the composite band two-dimensional image CGH0 in the high frequency band Hf as in the fourth embodiment. Meanwhile, in the medium-low frequency band MLf, the combination unit 34 generates the composite band two-dimensional image CGML0 in the medium-low frequency band MLf as in the fifth embodiment.

Meanwhile, in a case in which the band tomographic image is selected as in the sixth embodiment and the process according to the second embodiment is performed, the combination unit 34 generates the second composite band two-dimensional image CGH21 in the high frequency band Hf for the tumor as in the fourth embodiment. Meanwhile, in the medium-low frequency band MLf, the combination unit 34 generates the composite band two-dimensional image CGML21 in the medium-low frequency band MLf for the tumor as in the fifth embodiment.

Further, in each of the above-described embodiments, for the pixels in which the structure of interest is not detected, in a case in which the composite band two-dimensional image is generated from the band tomographic images, the added average value of the corresponding pixels of the band tomographic images is set as the pixel values of the composite band two-dimensional image. However, the present disclosure is not limited thereto. Furthermore, in the second and third embodiments, in a case in which the first composite two-dimensional image CG1 is generated, the added average value of the pixel values of the corresponding pixels of the tomographic image Dj is used as the pixel values of the first composite two-dimensional image CG1. However, the present disclosure is not limited thereto. Further, in the second and third embodiments, in a case in which the second composite band two-dimensional image CGML22 in the medium-low frequency band MLf for the spicula and the calcification is generated, the added average value of the pixel values of the corresponding pixels of the band tomographic images DMLj is set as the pixel values of the second composite band two-dimensional image CGML22. However, the present disclosure is not limited thereto. For example, other known techniques that use a weighted average value, a median value, or the like as the pixel value can be applied. Further, a minimum intensity projection method using the minimum value of the corresponding pixels in each band tomographic image or each tomographic image or a maximum intensity projection method using the maximum value may be used. In this case, a band tomographic image or a tomographic image including a pixel having the minimum value or the maximum value is a predetermined tomographic image according to the present disclosure.

In addition, for the pixels in which the structure of interest is not detected, the average value of the corresponding pixels in each band tomographic image or each tomographic image may be derived, a pixel having a value whose difference from the average value is smaller than a predetermined set value may be regarded as a noise pixel that is greatly affected by noise, and the pixel values of the composite band two-dimensional image or the composite two-dimensional image may be derived excluding the noise pixel. Further, for the corresponding pixels in each band tomographic image or each tomographic image, a variance value of pixel values in a predetermined region including the pixels may be derived, a pixel having a variance value that is smaller than a predetermined set value may be regarded as a noise pixel, and the pixel values of the composite band two-dimensional image or the composite two-dimensional image may be derived excluding the noise pixel. In this case, a band tomographic image or a tomographic image having pixels that are not the noise pixel is the predetermined tomographic image according to the present disclosure. Furthermore, a process that detects the edge of a structure included in each band tomographic image or each tomographic image may be performed. Then, for the pixels in which the structure of interest is not detected, the pixel values of the pixels including the edge may be used as the pixel values of the composite band two-dimensional image or the composite two-dimensional image. In this case, a band tomographic image or a tomographic image having the pixels including the edge is the predetermined tomographic image according to the present disclosure.

Further, in each of the above-described embodiments, all of the structures of interest of the tumor, the spicula, and the calcification are detected. However, the present invention is not limited thereto. The technology of the present disclosure can be applied even in a case in which at least one type of structure of interest among the tumor, the spicula, and the calcification is detected. In addition, in a case in which only one type of structure of interest is detected, the band tomographic image may be selected according to only the frequency band.

Further, the radiation in each of the above-described embodiments is not particularly limited. For example, α-rays or γ-rays can be applied in addition to the X-rays.

Furthermore, in each of the above-described embodiments, for example, the following various processors can be used as a hardware structure of processing units performing various processes, such as the image acquisition unit 30, the structure-of-interest detection unit 31, the frequency decomposition unit 32, the selection unit 33, the combination unit 34, and the display control unit 35. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. An image processing device comprising at least one processor,
   wherein the processor is configured to:
   detect a structure of interest from a plurality of tomographic images indicating a plurality of tomographic planes of an object;
   select a tomographic image from the plurality of tomographic images according to a frequency band in a region in which the structure of interest has been detected;
   generate a composite two-dimensional image using the selected tomographic image in the region in which the structure of interest has been detected and using a predetermined tomographic image in a region in which the structure of interest has not been detected;
   perform frequency decomposition on the plurality of tomographic images to derive a plurality of band tomographic images for each of a plurality of frequency bands, to select a band tomographic image corresponding to the tomographic image in which the structure of interest has been detected for each pixel, which corresponds to a pixel of the composite two-dimensional image, in the plurality of band tomographic images according to the frequency band; and
   generate the composite two-dimensional image using the selected band tomographic image in the region in which the structure of interest has been detected.

2. The image processing device according to claim 1,
   wherein the processor is configured to select different numbers of band tomographic images corresponding to the tomographic images in which the structure of interest has been detected from the plurality of band tomographic images according to the frequency band.

3. The image processing device according to claim 1,
   wherein the plurality of frequency bands include a first frequency band and a second frequency band lower than the first frequency band, and
   the processor is configured to select a smaller number of band tomographic images in the first frequency band than that in the second frequency band.

4. The image processing device according to claim 3,
   wherein the processor is configured to select all of the band tomographic images including the structure of interest for each pixel, which corresponds to a pixel of the composite two-dimensional image, in the plurality of band tomographic images in the second frequency band.

5. The image processing device according to claim 3,
   wherein the processor is configured to select one band tomographic image that best represents the structure of interest for each pixel, which corresponds to a pixel of the composite two-dimensional image, in the plurality of band tomographic images in the second frequency band.

6. The image processing device according to claim 5,
   wherein the one band tomographic image that best represents the structure of interest is a band tomographic image having a largest structure of interest or a band tomographic image having a highest likelihood in a case in which the structure of interest is detected.

7. The image processing device according to claim 3,
   wherein the processor is configured to select one band tomographic image that best represents the structure of interest for each pixel position, which corresponds to a pixel position of the composite two-dimensional image, in the plurality of band tomographic images in the first frequency band.

8. The image processing device according to claim 1,
   wherein the processor further selects the band tomographic image according to a type of the structure of interest.

9. The image processing device according to claim 8,
   wherein the structure of interest is a tumor, a spicula, and a calcification.

10. The image processing device according to claim 8,
    wherein the processor is configured to combine the plurality of tomographic images to generate a first composite two-dimensional image, to generate a composite band two-dimensional image for each frequency band using the band tomographic image selected for each type of the structure of interest in a pixel of the band tomographic image corresponding to the structure of interest, to perform frequency synthesis on the composite band two-dimensional images to generate a second composite two-dimensional image for each type of the structure of interest; and
    combine the second composite two-dimensional image generated for each type of the structure of interest with the first composite two-dimensional image to generate the composite two-dimensional image.

11. The image processing device according to claim 10,
    wherein the processor is configured to replace a pixel value of the structure of interest in the first composite two-dimensional image with a pixel value of the structure of interest in the second composite two-dimensional image to combine the second composite two-dimensional image with the first composite two-dimensional image.

12. The image processing device according to claim 11, wherein the processor is configured to generate the composite two-dimensional image having a pixel value of the second composite two-dimensional image determined on the basis of a predetermined priority of the structure of interest in a case in which a plurality of types of the structures of interest are included in corresponding pixels of the plurality of second composite two-dimensional images.

13. The image processing device according to claim 8, wherein the processor is configured to combine the plurality of tomographic images to generate a first composite two-dimensional image;
to extract a region of a predetermined specific type of structure of interest from the first composite two-dimensional image; and
generate a composite band two-dimensional image for each frequency band, using the band tomographic image selected for each of types of structures of interest other than the specific type of structure of interest, in pixels of the band tomographic image which correspond to the other structures of interest, to perform frequency synthesis on the composite band two-dimensional images to generate a second composite two-dimensional image for each type of the other structures of interest, to combine the second composite two-dimensional images for the other structures of interest with the first composite two-dimensional image, and to combine the region of the specific type of structure of interest with the first composite two-dimensional image, with which the second composite two-dimensional images have been combined, to generate the composite two-dimensional image.

14. The image processing device according to claim 13, wherein the specific structure of interest is a calcification, and the other structures of interest are a tumor and a spicula.

15. The image processing device according to claim 13, wherein the processor is configured to replace a pixel value of the structure of interest in the first composite two-dimensional image with a pixel value of the structure of interest in the second composite two-dimensional image to combine the second composite two-dimensional image with the first composite two-dimensional image.

16. The image processing device according to claim 15, wherein the processor is configured to generate the composite two-dimensional image having a pixel value of the second composite two-dimensional image determined on the basis of a predetermined priority of the structure of interest in a case in which a plurality of types of the other structures of interest are included in corresponding pixels of the plurality of second composite two-dimensional images.

17. The image processing device according to claim 13, wherein the processor is configured to replace a pixel value of the structure of interest in the first composite two-dimensional image, with which the second composite two-dimensional image has been combined, with a pixel value of the region of the specific type of structure of interest to combine the region of the specific type of structure of interest with the first composite two-dimensional image with which the second composite two-dimensional image has been combined.

18. The image processing device according to claim 1, wherein the processor is configured to generate a composite band two-dimensional image for each frequency band using the selected band tomographic image in a pixel of the band tomographic image corresponding to the structure of interest and to perform frequency synthesis on the composite band two-dimensional images to generate the composite two-dimensional image.

19. The image processing device according to claim 18, wherein the processor is configured to generate the composite band two-dimensional image that has a pixel value of a band tomographic image determined on the basis of a predetermined priority of the structure of interest in a case in which a plurality of the band tomographic images are selected in pixels, which correspond to a pixel of the composite band two-dimensional image, in the plurality of band tomographic images.

20. An image processing method comprising:
detecting a structure of interest from a plurality of tomographic images indicating a plurality of tomographic planes of an object;
selecting a tomographic image from the plurality of tomographic images according to a frequency band in a region in which the structure of interest has been detected;
generating a composite two-dimensional image using the selected tomographic image in the region in which the structure of interest has been detected and using a predetermined tomographic image in a region in which the structure of interest has not been detected;
performing frequency decomposition on the plurality of tomographic images to derive a plurality of band tomographic images for each of a plurality of frequency bands, to select a band tomographic image corresponding to the tomographic image in which the structure of interest has been detected for each pixel, which corresponds to a pixel of the composite two-dimensional image, in the plurality of band tomographic images according to the frequency band; and
generating the composite two-dimensional image using the selected band tomographic image in the region in which the structure of interest has been detected.

21. A non-transitory computer-readable storage medium that stores an image processing program that causes a computer to execute:
a procedure of detecting a structure of interest from a plurality of tomographic images indicating a plurality of tomographic planes of an object;
a procedure of selecting a tomographic image from the plurality of tomographic images according to a frequency band in a region in which the structure of interest has been detected;
a procedure of generating a composite two-dimensional image using the selected tomographic image in the region in which the structure of interest has been detected and using a predetermined tomographic image in a region in which the structure of interest has not been detected;
a procedure of performing frequency decomposition on the plurality of tomographic images to derive a plurality of band tomographic images for each of a plurality of frequency bands, to select a band tomographic image corresponding to the tomographic image in which the structure of interest has been detected for each pixel, which corresponds to a pixel of the composite two-dimensional image, in the plurality of band tomographic images according to the frequency band; and
a procedure of generating the composite two-dimensional image using the selected band tomographic image in the region in which the structure of interest has been detected.

* * * * *